(12) United States Patent
Taylor et al.

(10) Patent No.: US 7,434,781 B2
(45) Date of Patent: Oct. 14, 2008

(54) REMOTELY ACTUATED QUICK CONNECT/DISCONNECT COUPLING

(76) Inventors: Thomas M. Taylor, 481 Carica Rd., Naples, FL (US) 34108; David Goslin, 6118 Country Club Pkwy., Lehigh Acres, FL (US) 33972

( * ) Notice: Subject to any disclaimer, the term of this patent is extended or adjusted under 35 U.S.C. 154(b) by 64 days.

(21) Appl. No.: 10/856,035

(22) Filed: May 28, 2004

(65) Prior Publication Data

US 2004/0252556 A1    Dec. 16, 2004

Related U.S. Application Data

(60) Provisional application No. 60/474,467, filed on May 31, 2003.

(51) Int. Cl.
F16K 51/00 (2006.01)
F16L 29/00 (2006.01)

(52) U.S. Cl. .................... 251/148; 251/293; 285/312

(58) Field of Classification Search ............ 251/148, 251/293; 285/38, 312
See application file for complete search history.

(56) References Cited

U.S. PATENT DOCUMENTS

| | | |
|---|---|---|
| 1,018,251 A | 2/1912 | McKee |
| 1,086,841 A | 2/1914 | Mueller |
| RE21,470 E | 5/1940 | White |
| 2,752,307 A | 6/1956 | Baran et al. |
| 2,931,382 A | 4/1960 | Cirillo |
| 3,095,893 A | 7/1963 | Martin |
| 3,103,946 A | 9/1963 | Troxell |
| 3,283,776 A | 11/1966 | Flanagan et al. |
| 3,391,790 A | 7/1968 | Lerner |
| 3,592,212 A | 7/1971 | Schleimer |
| 3,682,311 A | 8/1972 | Bishop |
| 3,962,733 A | 6/1976 | Parry |
| 3,980,096 A | 9/1976 | Ellis et al. |
| 3,993,561 A | 11/1976 | Swearingen |
| 4,002,566 A | 1/1977 | Smith |
| 4,083,377 A | 4/1978 | Luckenbill |
| 4,154,259 A | 5/1979 | Ellis et al. |
| 4,165,532 A | 8/1979 | Kendall et al. |

(Continued)

FOREIGN PATENT DOCUMENTS

| | | |
|---|---|---|
| FR | 2 715 986 | 8/1995 |
| FR | 2 754 554 | 4/1998 |

OTHER PUBLICATIONS

European Patent Office: Supplementary European Search Report, dated Oct. 25, 2006.

(Continued)

*Primary Examiner*—John K. Fristoe, Jr.
(74) *Attorney, Agent, or Firm*—Akerman Senterfitt

(57) ABSTRACT

A water flushing system for a pressurized subterranean water distribution system includes an inlet conduit for receiving pressurized water from the subterranean water distribution system; an outlet fluidly connected to the inlet conduit for discharging pressurized water in the inlet conduit downwardly towards a drain; and a control valve for controlling the flow of pressurized water in the inlet conduit. The water flushing system further includes one or more of the following features: a freeze protection assembly, a detachable coupling system, a dechlorination system, and a backflow prevention system.

10 Claims, 19 Drawing Sheets

U.S. PATENT DOCUMENTS

| | | | |
|---|---|---|---|
| 4,182,361 | A | 1/1980 | Oakey |
| 4,189,776 | A | 2/1980 | Kendall |
| 4,212,424 | A | 7/1980 | Fortune |
| 4,216,185 | A | 8/1980 | Hopkins |
| RE31,023 | E | 9/1982 | Hall, III |
| 4,373,838 | A | 2/1983 | Foreman et al. |
| 4,393,891 | A | 7/1983 | Snoek et al. |
| 4,483,189 | A | 11/1984 | Seal |
| 4,556,080 | A | 12/1985 | Picaud |
| 4,575,130 | A * | 3/1986 | Pemberton et al. ............ 285/38 |
| 4,615,390 | A | 10/1986 | Lucas et al. |
| 4,639,718 | A | 1/1987 | Gasper |
| 4,653,521 | A | 3/1987 | Fillman |
| 4,676,914 | A | 6/1987 | Mills et al. |
| 4,721,408 | A | 1/1988 | Hewlett |
| 4,756,479 | A | 7/1988 | Lazenby, III |
| 4,774,978 | A | 10/1988 | Lepine, Jr. et al. |
| 4,799,142 | A | 1/1989 | Waltzer et al. |
| 4,816,154 | A | 3/1989 | Hartley |
| 4,838,485 | A | 6/1989 | Rinkewich |
| 4,876,530 | A | 10/1989 | Hill et al. |
| 4,898,107 | A | 2/1990 | Dickinson |
| 5,002,428 | A | 3/1991 | Shettel |
| 5,011,598 | A | 4/1991 | Nathanson |
| 5,025,754 | A | 6/1991 | Plyler |
| 5,032,290 | A | 7/1991 | Yamagata et al. |
| 5,042,524 | A | 8/1991 | Lund |
| RE33,723 | E | 10/1991 | Hartley |
| 5,115,833 | A | 5/1992 | Himle |
| 5,133,622 | A | 7/1992 | Hewlett |
| 5,136,983 | A | 8/1992 | Hostetler et al. |
| 5,176,165 | A | 1/1993 | Traylor |
| 5,184,571 | A | 2/1993 | Hostetler et al. |
| 5,201,338 | A | 4/1993 | McKeague |
| 5,227,067 | A | 7/1993 | Runyon |
| 5,227,068 | A | 7/1993 | Runyon |
| 5,240,179 | A | 8/1993 | Drinkwater |
| 5,249,745 | A | 10/1993 | Berlotti |
| 5,261,348 | A | 11/1993 | Niehaus et al. |
| 5,264,368 | A | 11/1993 | Clarke et al. |
| 5,314,619 | A | 5/1994 | Runyon |
| 5,324,665 | A | 6/1994 | Lessard |
| 5,331,694 | A | 7/1994 | Mackenzie et al. |
| 5,332,494 | A | 7/1994 | Eden et al. |
| 5,351,712 | A | 10/1994 | Houlihan |
| 5,360,488 | A | 11/1994 | Hieatt et al. |
| 5,368,227 | A | 11/1994 | McGinnis |
| 5,368,343 | A * | 11/1994 | Allen ........................ 285/312 |
| 5,479,338 | A | 12/1995 | Ericksen et al. |
| 5,480,562 | A | 1/1996 | Lemelson |
| 5,490,561 | A | 2/1996 | Cardoso-Neto et al. |
| 5,527,470 | A | 6/1996 | Suda |
| 5,535,984 | A * | 7/1996 | Anderson et al. ........ 251/149.9 |
| 5,540,845 | A | 7/1996 | Blanchard et al. |
| 5,549,133 | A | 8/1996 | Sigelakis |
| 5,553,637 | A | 9/1996 | Hoeptner, III |
| 5,582,440 | A * | 12/1996 | Pascaru ..................... 285/373 |
| 5,587,055 | A | 12/1996 | Hartman et al. |
| 5,609,124 | A | 3/1997 | Leclerc |
| 5,623,990 | A | 4/1997 | Pirkle |
| 5,645,011 | A | 7/1997 | Winkler et al. |
| 5,746,923 | A | 5/1998 | Forward |
| 5,775,372 | A | 7/1998 | Houlihan |
| 5,797,417 | A | 8/1998 | DeLattre et al. |
| 5,803,111 | A | 9/1998 | Soszka |
| 5,813,363 | A | 9/1998 | Snelling |
| 5,817,231 | A | 10/1998 | Souza |
| 5,829,475 | A | 11/1998 | Acker |
| 5,865,991 | A | 2/1999 | Hsu |
| 5,885,364 | A | 3/1999 | Hieatt et al. |
| 5,915,395 | A | 6/1999 | Smith |
| 5,921,207 | A | 7/1999 | DiSalvo et al. |
| 5,921,270 | A | 7/1999 | McCarty |
| 5,979,482 | A | 11/1999 | Scott |
| 5,996,608 | A | 12/1999 | Hunter et al. |
| 6,003,780 | A | 12/1999 | Gurries, II et al. |
| 6,035,704 | A | 3/2000 | Newman |
| 6,044,911 | A | 4/2000 | Haase, III |
| 6,056,211 | A | 5/2000 | DiLoreto |
| 6,062,259 | A | 5/2000 | Poirier |
| 6,062,606 | A * | 5/2000 | Carpini et al. ................ 285/38 |
| 6,063,275 | A | 5/2000 | Traylor |
| 6,095,429 | A | 8/2000 | Killgrove et al. |
| 6,116,525 | A | 9/2000 | Grimes |
| 6,170,514 | B1 | 1/2001 | Esmailzadeh |
| 6,221,257 | B1 | 4/2001 | Grim |
| 6,227,463 | B1 | 5/2001 | Porter |
| 6,227,464 | B1 | 5/2001 | Allmendinger et al. |
| 6,290,267 | B1 * | 9/2001 | Swingley .................... 285/312 |
| 6,294,096 | B1 | 9/2001 | Pate |
| 6,358,408 | B1 | 3/2002 | Newman |
| 6,385,794 | B1 | 5/2002 | Miedzius et al. |
| 6,467,498 | B1 | 10/2002 | Esmailzadeh |
| 6,491,062 | B1 * | 12/2002 | Croft ..................... 137/624.11 |
| 6,520,431 | B2 | 2/2003 | Donovan |
| 6,524,681 | B1 | 2/2003 | Seitz et al. |
| 6,635,172 | B2 | 10/2003 | Newman |
| 6,684,900 | B1 | 2/2004 | McKeague |
| 6,711,758 | B1 | 3/2004 | Terek et al. |
| 6,820,635 | B1 | 11/2004 | McKeague |
| 6,880,566 | B2 | 4/2005 | Newman |
| 6,948,512 | B2 | 9/2005 | McKeague |
| 2002/0029412 | A1 | 3/2002 | Veal |
| 2002/0053104 | A1 | 5/2002 | Rump et al. |
| 2002/0069457 | A1 | 6/2002 | Meier et al. |
| 2002/0073482 | A1 | 6/2002 | Hashemi |
| 2002/0092090 | A1 | 7/2002 | Johnson |
| 2002/0117214 | A1 | 8/2002 | Tucker et al. |
| 2002/0144952 | A1 | 10/2002 | Saxton |
| 2002/0157176 | A1 | 10/2002 | Wawrla et al. |
| 2002/0157708 | A1 | 10/2002 | Goff |
| 2002/0162166 | A1 | 11/2002 | Saar et al. |
| 2002/0194670 | A1 | 12/2002 | Hashemi |
| 2003/0041370 | A1 | 3/2003 | Chung |
| 2003/0057155 | A1 | 3/2003 | Husain et al. |
| 2003/0066125 | A1 | 4/2003 | Guler |
| 2003/0102450 | A1 | 6/2003 | Parsons et al. |
| 2003/0155443 | A1 | 8/2003 | Ace-Kirker |
| 2003/0193036 | A1 | 10/2003 | Mike |
| 2004/0031446 | A1 | 2/2004 | Harrison |
| 2004/0054484 | A1 | 3/2004 | Farabaugh et al. |
| 2004/0054851 | A1 | 3/2004 | Acton et al. |
| 2004/0068784 | A1 | 4/2004 | Muderlak |
| 2004/0143893 | A1 | 7/2004 | Wu et al. |

OTHER PUBLICATIONS

European Patent Office: Communication Pursuant to Article 96(2) EPC & Examination Report, dated Sep. 10, 2007 (Appln. No. 99 927 502.7).

Response to Article 96(2) EPC Communication, dated Mar. 11, 2008.

Complaint, dated Nov. 14, 2006, *Environmental Enhancement & Technologies, Inc.* v. *John C. Kupferle Foundry Company.*

First Amended Complaint, dated Dec. 28, 2006, *Environmental Enhancement* v. *Kupferle et al.*, Case No. 6:06-CV-1754-ORL-JA-DAB.

Agreed Upon Motion for a Third Extension of Time in Which to Respond to Plaintiff's Complaint, dated Mar. 27, 2007.

Order of Dismissal Without Prejudice, Feb. 5, 2007.

The Toro Company: Toro Remote 1000 Series Battery-Operated Valve Controller, dated May 2000.

The Toro Company: Remote 1000 / 2000 / 3000 Individual Valve Controller User's Guide, copyright 1999.

Letter from J. Phillip Polster to Jerold I. Schneider, dated Feb. 6, 2007 (includes 4 pages of attachments).

Photographs (7) taken by Kristen L. Wood in Apr. 2007 in Lousiana during visit with Mr. Jimmy French, includes photos of a McCarty device and Record Book.

Diehl Controls: Built-in Timer Series 884, date unknown but indicates as being updated in Feb. 2004.

Photographs (5) taken by Kristen L. Wood in Apr. 2007 in Lousiana during visit with Mr. Arnold Brewer, includes photos of a McCarty device.

Photographs (6) taken by Kristen L. Wood in Apr. 2007 in Lousiana during visit with Mr. James Byrd, includes photos of a first McCarty device.

Photographs (7) taken by Kristen L. Wood in Apr. 2007 in Lousiana during visit with Mr. James Byrd, includes photos of a second McCarty device.

CD with video taken by Kristen L. Wood in Apr. 2007 in Lousiana during visit with Mr. James Byrd, showing the first McCarty device.

* cited by examiner

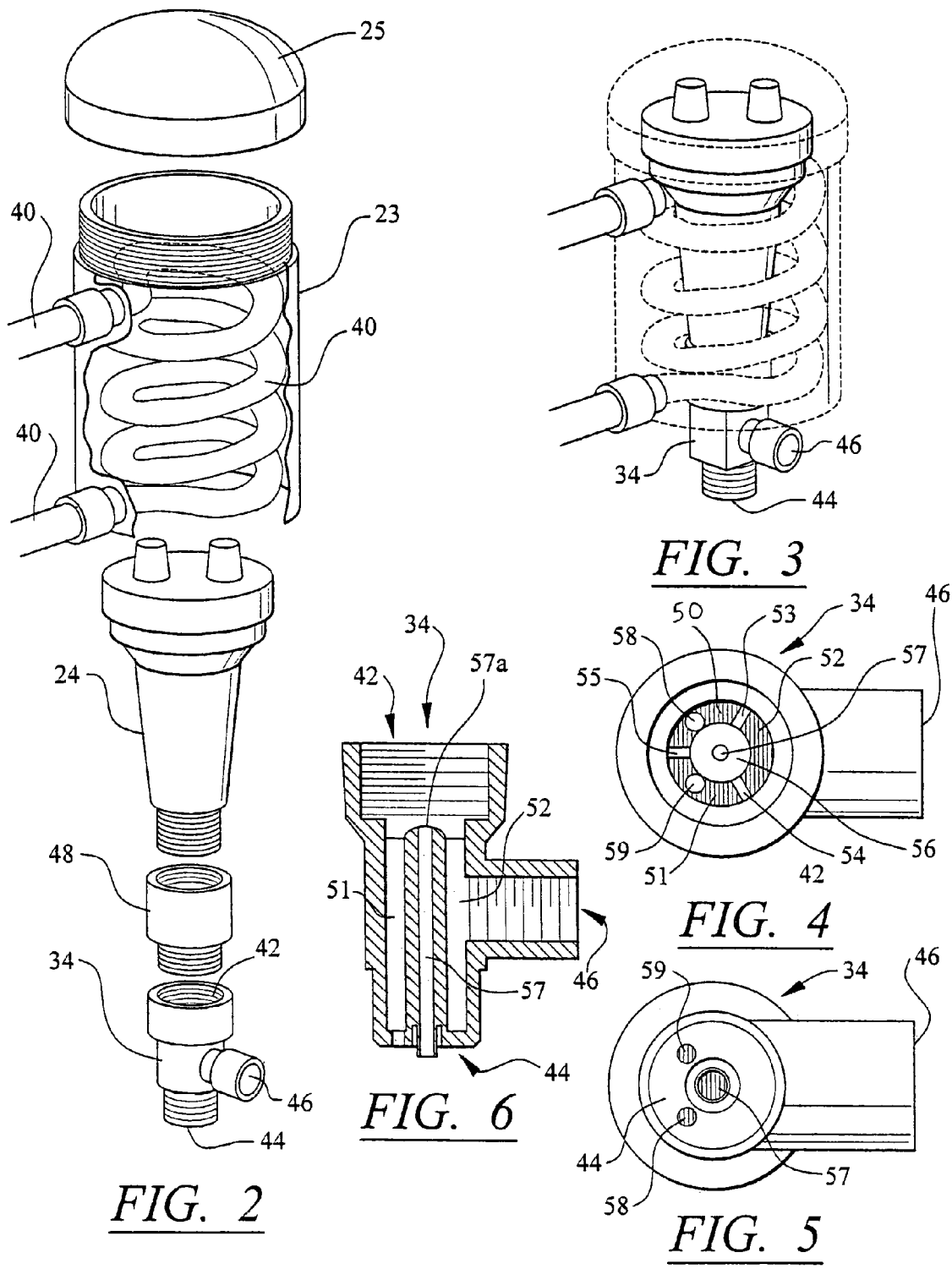

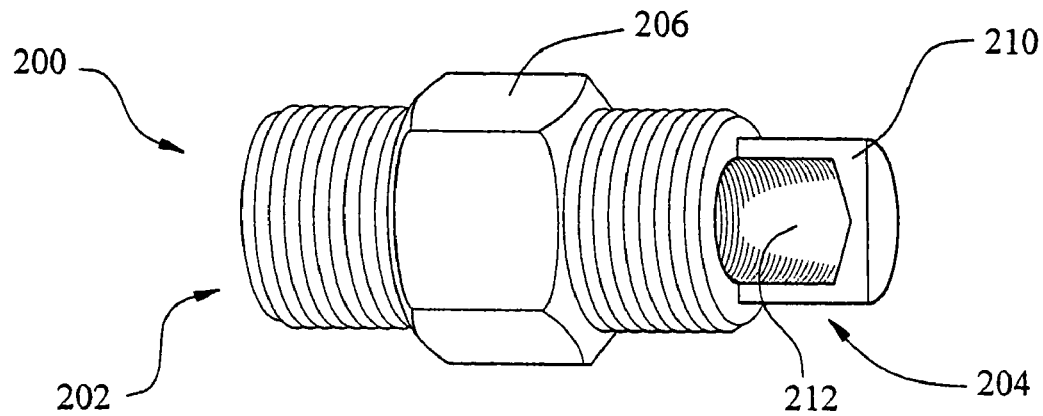
FIG. 21
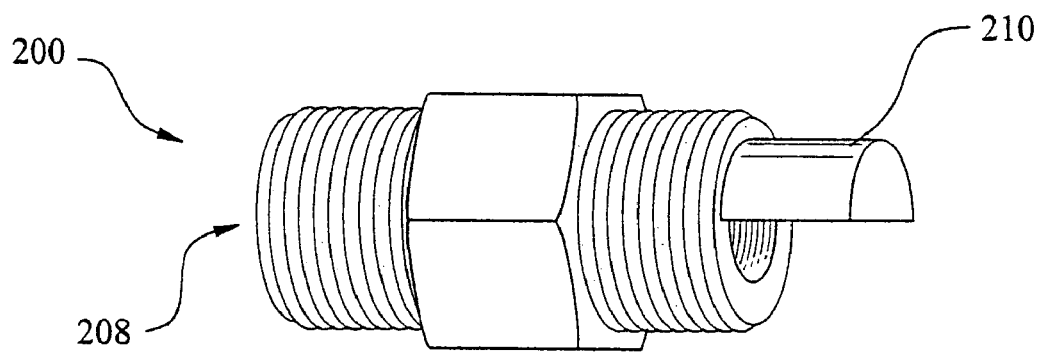
FIG. 22
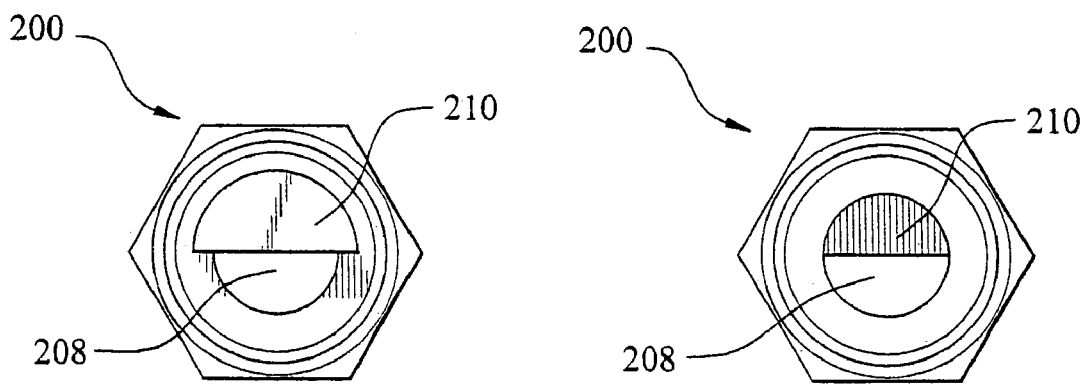
FIG. 23
FIG. 24

REMOTELY ACTUATED QUICK CONNECT/DISCONNECT COUPLING

CROSS-REFERENCE TO RELATED APPLICATIONS

This Application claims the benefit of U.S. Provisional Application No. 60/474,467, filed on May 31, 2003.

FIELD OF THE INVENTION

The invention relates in general to water quality maintenance devices and systems and, more particularly, to a water flushing apparatus for automatically maintaining water quality in a water distribution system.

BACKGROUND OF THE INVENTION

Water flushing systems are known in the art such as those disclosed in U.S. Pat. Nos. 6,358,408 and 6,035,704. While the main purpose of these systems is to improve water quality in a water distribution system, such systems can include a number of auxiliary features that address specific issues relating to water flushing systems.

For instance, some water flushing systems are used in locations that may expose the system to subfreezing temperatures. Such environments can be damaging to various components of the system. For example, when the water contained in a pipe freezes, it expands and may ultimately break the surrounding pipe. Moreover, frigid conditions can interfere with the proper functioning of a water flushing system. Some flushing systems use electronic controls to automatically open and close various valves. However, many of these electronic devices are sensitive to temperature extremes and, in subfreezing climates, the electronic unit may become inoperative. Accordingly, there is a need for a water quality apparatus that can protect various components against the potential dangers caused by freezing temperatures.

Another problem associated with water flushing systems is the backward flow of contaminated or otherwise unclean water into the water distribution system. Thus, it is desirable to provide a water flushing system that prevents backflow of contaminated water into the water distribution system.

Further, some jurisdictions may impose environmental or other requirements on water discharged from the flushing system. For example, a municipality may prohibit the discharge of chlorinated water into the ground or into a storm drain. Therefore, it is desirable for a water flushing apparatus to provide a system or device for appropriately treating at least a portion of the water discharged from the system such as by providing a dechlorination system.

Still another issue concerns the accessibility of water flushing systems in which most of the operating components are disposed below grade level and/or water flushing systems that are enclosed within any confined space. Because such systems may require regular inspection and maintenance, not to mention occasional repairs, there is a need to provide a system that permits retrieval and/or access to a substantial portion of the water flushing apparatus in a relatively expeditious manner.

Thus, one object according to aspects of the present invention is to provide a water flushing system that includes freeze protection features. Another object according to aspects of the invention is to provide a water flushing apparatus having backflow prevention attributes. Still another object according to aspects of the invention is to provide a device or system for dechlorination or other treatment of water exiting the system.

Yet another object according to aspects of the invention is to provide an apparatus and method for retrieving a water flushing system disposed in a confined space. These and other objects according to aspects of the present invention are addressed below.

SUMMARY OF THE INVENTION

A water flushing system for a pressurized subterranean water distribution system includes an inlet conduit for receiving pressurized water from the subterranean water distribution system; an outlet fluidly connected to the inlet conduit for discharging pressurized water in the inlet conduit; and a control valve for controlling the flow of pressurized water in the inlet conduit. The flushing system can further include one or more of the following: a freeze protection assembly, a detachable coupling system and method, a water treatment system such as a dechlorination system, and a backflow prevention system.

BRIEF DESCRIPTION OF THE DRAWINGS

FIG. 2 is an exploded isometric view of a programmable controller for controlling a flow control valve according to aspects of the present invention.

FIG. 3 is an isometric view of a controller disposed within a housing according to aspects of the present invention.

FIG. 4 is a top plan view of a t-fitting according to aspects of the present invention.

FIG. 5 is a bottom plan view of a t-fitting according to aspects of the present invention.

FIG. 6 is a cross-sectional view of a t-fitting according to aspects of the present invention.

FIG. 21 is an isometric view of a fitting according to aspects of the present invention.

FIG. 22 is an isometric view of a fitting according to aspects of the present invention.

FIG. 23 is a side elevational view of a fitting according to aspects of the present invention.

FIG. 24 is a side elevational view of a fitting according to aspects of the present invention.

DETAILED DESCRIPTION OF EMBODIMENTS OF THE INVENTION

Aspects of the present invention address many of the problems relating to water flushing systems. More particularly, aspects according to the present invention relate to freeze protection, backflow prevention, and dechlorination or other water treatment in connection with water flushing systems. Other aspects of the present invention are directed to an apparatus and methods for allowing a user to remotely retrieve an apparatus or system including a water flushing system. These aspects and other aspects will be discussed in connection with various water flushing systems.

Embodiments of the invention will be explained in the context of various water flushing systems, but the detailed description is intended only as exemplary. Embodiments according to aspects of the invention are shown in FIGS. 1-39, but the present invention is not limited to the illustrated structure or application.

Water flushing systems can have a variety of configurations and arrangements. Examples of such systems are shown in FIGS. 1, and 9-15. The system shown in FIGS. 9-15 will generally and/or collectively be referred to as column-type systems; the system shown in FIG. 1 will generally be referred to as a box-type system. The terms "column" and "box" are given only to facilitate discussion and are not intended to limit the scope of the invention to any particular layout. While each of these systems can be arranged in different manners, many of the individual components are common between the various systems. Both the box-type system and the column-type system will be discussed in turn according to aspects of the present invention.

Figure 1:
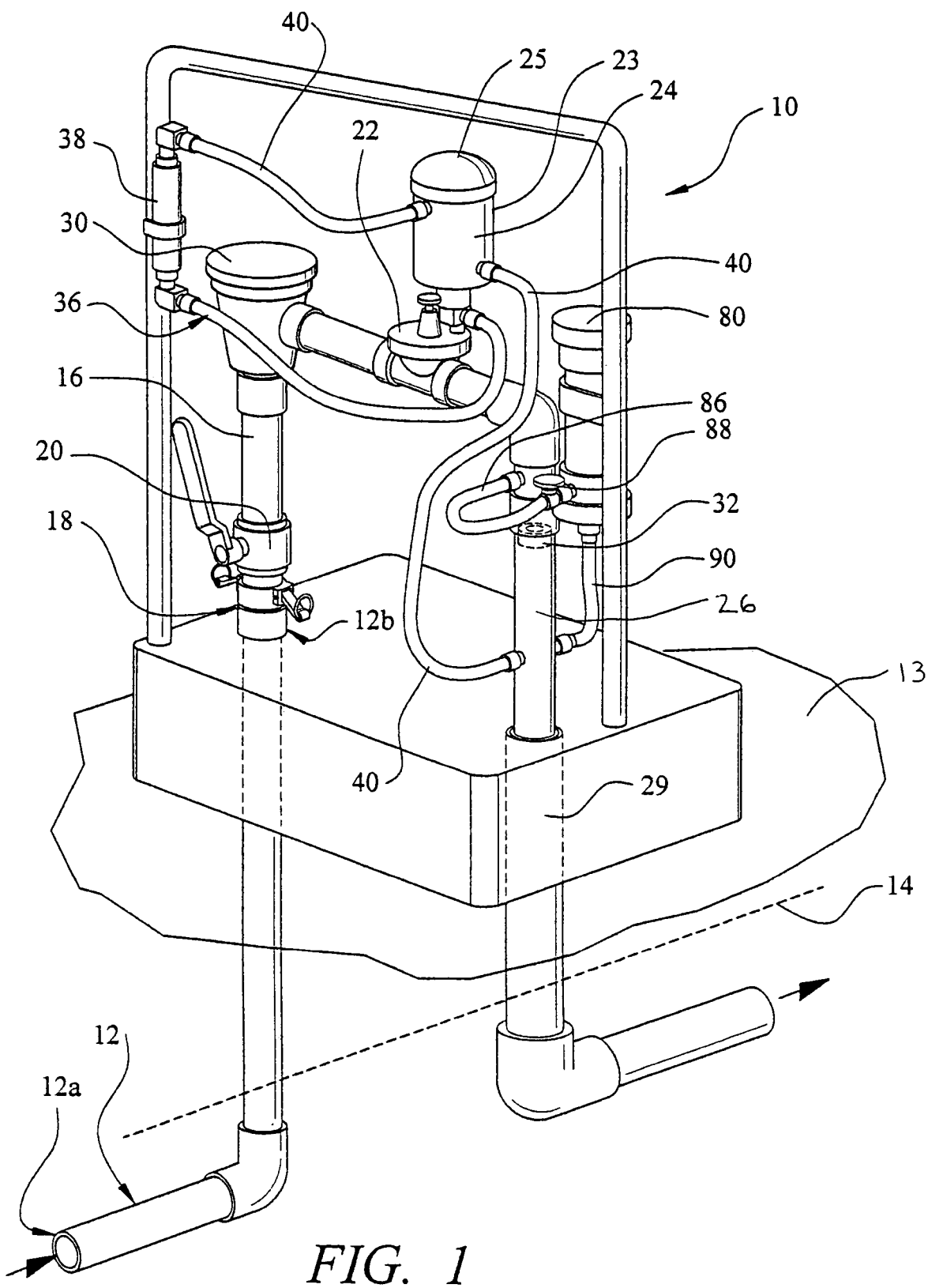
FIG. 1 is an isometric view of a water flushing apparatus according to aspects of the present invention.

An example of a box-type water flushing system 10 is shown in FIG. 1. The system includes water carrier piping 12 that connects to a pressurized subterranean water distribution system (not shown), which can be located below the ground level 13, preferably below the freeze or frost line 14 of the ground. The dimensions and configuration of the water carrier piping 12 are adapted for connection to the particular piping or provisions of the water distribution system. For example, the inlet end 12a of the water carrier piping can provide a male or a female connector that can be threaded for threaded engagement with the water distribution system. The water carrier piping 12 can comprise a single pipe, which can be straight or include one or more bends, or it can comprise a plurality of pipes and/or fittings.

Regardless of the exact configuration, the water carrier piping 12 is generally connected at its inlet end 12a to the water distribution system and at its outlet end 12b to other components of the water flushing system 10. The outlet end 12b of the water carrier piping 12 can be connected to the other components of the water flushing system 10 in various manners such as by threaded engagement, adhesives, fasteners or welding. Preferably, the water flushing system 10 and the water carrier piping 12 are detachably coupled together by a quick connect/disconnect device 18 such as a cam lock. An example of a cam lock device is illustrated in FIGS. 27-30 and is discussed later.

In one embodiment, the water carrier piping 12 can be detachably coupled to a flow controlled passage 16 of the water flushing system 10. The flow controlled passage 16 can comprise a single pipe or a plurality of pipe segments and/or fittings. Under certain circumstances, it may be desirable to completely cut off water flow to the apparatus. For instance, isolation may be desirable when the apparatus is undergoing repair. Thus, an isolation or shut-off valve 20 for controlling the introduction of water into the apparatus can be disposed along the flow controlled passage.

Water entering the flow controlled passage 16 can encounter a flow control valve 22. The flow control valve 22 can control the rate at which water is purged from the system. When not in a flushing mode, the flow control valve 22 can completely restrict the flow of the incoming water from the main line. The flow control valve 22 can be any type of valve such as a ball valve. Preferably, the flow control valve 22 is capable of passing sand and other debris without obstructing the valve 22. The flow control valve 22 can be constructed of various materials including metals and plastics such as non-corrosive glass reinforced nylon.

A programmable controller 24 can be provided for activating and deactivating the flow control valve 22. Thus, the controller 24 can be programmed to activate the flow control valve 22 in various settings or cycles. For example, the controller 24 can be set for a specific day, at a desired time of day and/or for a specified duration of time. In one embodiment, the controller 24 can be integrated with the flow control valve 22. The programmable controller 24 can be a solenoid controller. Preferably, the controller 24 can be powered by a power supply such as a replaceable self-contained power source like a 9-volt battery. Ideally, the power source can have an operating life of about 8 months to 12 months under normal operating conditions.

The controller 24 can store instructions from a hand-held detachable programmer (not shown). Alternatively, the controller 24 can include a integral keypad or other user interface. The programmer can transmit instructions to the controller in numerous ways. In one embodiment, a programming/data retrieval port (not shown), such as a standard telephone handset jack, can be integral with the controller 24 or it can be integrated into a portion of the apparatus housing (not shown). The port and the controller can be separate pieces and, when they are, a cord can be provided to connect them together.

The port can be adapted for receiving instructions from a remote hand-held programming device (not shown). For instance, the hand-held programming device can comprise a lap-top computer. The hand-held electronic device can communicate programming instructions to the programmable controller 24 in various manners. The port can provide for either uni-directional or bi-directional communication between the programming device and the controller 24.

In basic operation, when the flow control valve 22 is opened, water in the flow controlled passage 16 can pass through the flow control valve 22 and into discharge piping 26. Discharge piping 26 preferably routs the water downward, such as into a receiving drain 29, so as to avoid the dangers associated with upward or lateral discharge.

The discharge piping 26 can be configured in several ways. It can be a single pipe or a plurality of pipes and/or fittings. The discharge piping 26 can comprise rigid pipes and/or flexible pipes overall or in certain portions. The discharge piping 26 can be in fluid communication with a receiving drain 29. In one embodiment, the discharge piping 26 can connect directly to a receiving drain 29. Such a connection can be made in various ways such as by any of a number of pipe fittings, hose clamps or a quick connect/disconnect device. Alternatively, the discharge piping 26 and the receiving drain 29 may not be directly connected. In one embodiment, an air gap can separate the discharge piping 26 and the receiving drain 29. Though the discharge piping 26 and the receiving drain 29 are no longer directly connected, they are in substantial fluid communication so that water exiting the discharge piping 26 can be substantially received in the receiving drain 29. The air gap configuration offers protection against backflow of contaminated or unclean water. With such a configuration, the box-type water flushing system 10 may not need any other backflow prevention devices as part of the system.

However, when no air gap is provided between the discharge piping 26 and the, receiving drain 29, backflow can still be an issue. Thus, aspects according to the invention relate to preventing the backflow of water in the water flushing system 10. In one aspect, the box-type water flushing system can include a backflow prevention device. The backflow prevention device can be any of a number of devices including an RPZ, which operates on a reduced pressure zone theory. Preferably, the backflow prevention device is a vacuum pressure breaker 30. Vacuum pressure breakers and RPZs are known in the art, so the details of their operation will not be explained as they are generally understood by one skilled in the art.

It has been observed that, during operation, the vacuum pressure breaker 30 may sometimes fail to close properly. Such a problem can be alleviated by applying a back pressure on the vacuum pressure breaker 30. To create the needed back pressure, the discharge piping 26 downstream of the vacuum pressure breaker 30 can be reduced to create a choked flow condition. For example, in one embodiment, the discharge piping 26 can be reduced from an inner diameter of about 2 inches to an inner diameter of about 1 inch.

The reduction can be accomplished in a variety of ways. For example, the discharge pipe 26 can have a specially contoured inner passage that can, for example, include a sharp reduction in inner diameter. Alternatively, the choked flow condition can be created by connecting pipe segments having unequal inner diameters. Further, as shown in FIG. 1, a separate piece such as a reducer 32 can be inserted into the discharge piping 26 downstream from the vacuum pressure breaker 30 to create the needed back pressure.

Figure 7:
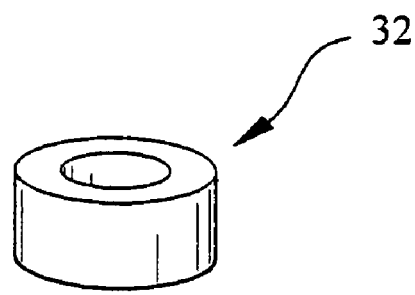
FIG. 7 is an isometric view of a reducer according to aspects of the present invention.

One possible configuration for a reducer appears in FIG. 7. As shown, the reducer 32 can be a generally cylindrical part having an outer diameter sized for receipt inside of the discharge piping 26. For example, if the discharge piping 26 has an inner diameter of approximately 2 inches, the reducer 32 can have an outer diameter of about 1⅞ inches. The inner diameter of the reducer 32 can be sized to create the desired choke flow condition. In one embodiment, the inner diameter of the reducer 32 can be about 1 inch. The reducer 32 can be placed inside of the discharge piping 26 either with or without the benefit of additional securement devices such as glue. The reducer 32 can be made of any material such as metals including brass, but plastics including PVC are preferred. When employed, the reducer 32 can increase the pressure in the portion of the discharge piping 26 prior to the reducer 32. Experience has demonstrated that this extra back pressure can facilitate closure of the vacuum pressure breaker.

Aspects of the present invention can further relate to a freeze protection system for the box systems to address the previously-described dangers of subfreezing temperatures. Before turning to the details of the present invention, the Applicants wish to describe a prior art freeze protection system that has been applied to box-type water flushing devices. In the prior art, a t-fitting was interposed between the controller and the flow control valve. Branching off from the t-fitting was a plastic tube that entered into the housing for the controller. Inside the housing, the plastic tube wrapped in coil-like fashion, extending downwardly about the inner periphery of the housing. The plastic tube exited near the bottom of the housing and then connected into a first end of a temperature control valve.

The second end of the temperature control valve was connected to outlet plastic tubing. This tubing ultimately tied into the discharge flow path of the system so as to be purged from the system. The temperature control valve measured the water temperature in the tubing connecting into the temperature control valve. The temperature control valve could further be set to fully or partly open at certain predetermined temperature levels. When the temperature control valve opened, there would be a decrease in the pressure in the tubing extending between the t-fitting and the temperature control valve. The decrease in pressure would cause the control valve to open a generally commensurate amount to allow water to flush through the apparatus.

This arrangement was designed to provide freeze protection by exchanging the near freezing water in the lines with warmer water from a subterranean water distribution system located below the frost line. Such replacement water would naturally be above the ambient freezing temperatures. The passage of the warmer water through the system would prevent the lines from freezing and, in addition, would circulate through the coiled line surrounding the controller so as to prevent the controller and associated electronics from freezing.

However, further study and field experience has revealed imperfections in the above-described arrangement. For example, the above-described arrangement can result in the thermal control valve measuring artificially warmer water temperatures in the incoming supply line. This water was indeed warmer because it had initially passed through the coiled tubing surrounding the controller. As noted earlier, the coiled tubing is contained within a housing, which acted as somewhat of a barrier from the external environment. Thus, the water leaving the coil and flowing up to the temperature control valve was warmer than, for example, water in other tubing in the system. But, since the temperature control valve only took readings from water in its incoming line, the temperature reading were not representative of the water temperature in other parts of the system.

Because the temperature control valve measured a higher temperature, it would remain closed and not allow warmer water from below ground to replace the freezing water. Consequently, the water would freeze before the temperature control valve opened. This problem may have been exacerbated by the size of plastic tubing used in the system. In this prior system, the tubing was ¼ inch in diameter. However, experience has demonstrated that water in tubing of that size is more likely to freeze compared to water in tubing of a somewhat larger diameter, such as ⅜ or ½ inches.

The problems associated with at least the above-described prior system are addressed according to aspects of the present invention. In one respect, the system components can be rearranged so as to avoid the artificially high temperature readings taken by the temperature control valve. In another respect, the system tubing can be replaced with larger diameter tubing to further impede the onset of freezing.

FIGS. 1-6 shows an example of a system and various individual components that can be arranged to provide an improved freeze protection system according to aspects of the present invention. The general arrangement will now be described. A t-fitting 34 can be inserted between the controller and the flow control valve. A first tube 36 can branch off from the t-fitting and can be routed directly to the inlet of the temperature control valve 38. At the outlet of the temperature control valve 38, a second tube 40 can be provided that to carry water into and out of a housing 23 for the controller 24. Specifically, as shown in FIGS. 2 and 3, the second tube 40 can enter the housing and coil around the inner periphery of the housing in a generally downward spiral path. The second tube 40 can be coiled in such a way so as to receive at least a portion of the controller 24. When the controller 24 is inserted into housing 23, at least a portion of the controller 24 can be substantially surrounded by the second tube 40.

After exiting the housing 23, the second tube 40 continues and connects into discharge piping 26. If a reducer 32 is used in the water flushing system 10, then it is preferred if the second tube 40 connects into the discharge piping 26 at a point downstream from the reducer 32. While the pressure in the discharge pipe 26 can be relatively high upstream of the reducer, the pressure can conversely be relatively low downstream of the reducer 32. Thus, by connecting the second tube 40 into the discharge piping 26 downstream of the reducer 32, the second tube can benefit from the low pressure, which may provide a suction effect to facilitate fluid flow through and out of second tube 40. Having described the basic arrangement of a freeze protection system according to aspects of the invention, the individual components will be discussed in turn below.

The t-fitting 34, among other things, facilitates the opening of the flow control valve for normal flushing and freeze protection purposes. An example of a t-fitting 34 that can have certain features according to aspects of the present invention is shown in FIGS. 4-6. The t-fitting has first 42, second 44 and third 46 ends. The first end 42 can be connected directly to the controller 24 such as by threaded engagement. However, the connection may be indirect as well. For example, as shown in FIG. 2, an adapter 48 can be disposed between the controller 24 and the t-fitting 34 for providing adaptability between the controller 24 and other components, if needed. Similarly, the second end 44 can connect, either directly or indirectly, into the flow control valve 22. The third end 46 can connect into the first tube 36 such as by hose clamps, fitting or a swage-type connection. Each of these ends 42,44,46 can have any of a number of configurations such as internal or external threads. Further, the configuration of the ends 42,44,46 can be identical to or completely different from each other. The t-fitting 34 can be made of any material such as metals or plastics.

The t-fitting 34 can have numerous internal features according to aspects of the present invention. For example, the t-fitting 34 can include three passages 50,51,52 that are generally defined by the inner diameter of the t-fitting 34 and three dividing walls 53,54,55 extending from a central hub 56. Extending through the central hub 56 is a passage 57. At the second end 44 of the t-fitting 34, each of passages 50,51 can include an opening 58,59, respectively. The above described features can cooperate to open and close the flow control valve 22.

Openings 58,59 provide a path for water to initially enter the t-fitting 34. However, any further flow is generally cut off by the flow control valve 22 and the temperature control valve 38. Further, in one embodiment, the upper opening 57a of the passage 57 can be sealing closed by a nipple and/or plunger (not shown) associated with the controller 24. In short, the water in and around the t-fitting 34 is generally under pressure, and the arrangement of the internal features of the t-fitting assist in the opening and closing of the flow control valve 22.

For example, during a normal flushing operation, the controller 24 can activate the flow control valve 22 by retracting the plunger/nipple so that it lifts off of the upper opening 57a. As a result, the pressurized water in the t-fitting 34 will flow into passage 57. This creates a loss of pressure in that region. In one embodiment, the flow control valve 22 can include diaphragm (not shown) that can be sensitive to pressure shifts. Thus, the loss of pressure created when the plunger/nipple was lifted off of the upper opening 57a causes the flow control valve to open and water is flushed from the water distribution system. In addition, water that flows into the passage 57 can flow out into the control valve on the other side of the diaphragm. To end the flushing cycle, the controller can push the plunger and/or nipple over the upper opening 57a of passage 57. Again, this is merely an example of one way in which the controller 24 can operate the flow control valve 22.

Not only can the controller 22 operate the flow control valve 24, but the temperature control valve 38 can operate the flow control valve as well, separately and independently from the controller 22. As will be described below, the temperature control valve 38 can create a pressure relief when it opens so as to cause the flow control valve 22 to open. Starting in a non-flushing mode, the first tube 36 is filled with water. Water is allowed to enter the first tube 36 through passage 46 in the t-fitting 34. Thus, a portion of the water in the first tube 36 is substantially proximate to the temperature control valve 38. When the water in the first tube 36 reaches a certain temperature (as discussed below), the temperature control valve 38 opens, which relieves the pressure in the first tube 36 so as to allow water to flow through the temperature control valve 38.

The pressure loss causes more water to be delivered to the first tube 36 through the t-fitting 34. As a result, the flow control valve will open 22 and the system will begin a flush cycle. The above is merely one example of t-fitting; there are a variety of t- and other type fittings or other fitting within the scope of the invention.

Aside from the t-fitting, there are several other components that can be a part of the freeze protection system according to aspects of the invention such as the housing 23 for the controller 24. The housing 23 can have a variety of configurations. For example, the housing 23 can be generally cylindrical and at least one of its ends 23a,23b can be open. The housing 23 can have any shape so long as it can accommodate the controller 24 and the coiled second tube 40. In one embodiment, the housing can include one or more openings for accommodating the second tube as it enters and exits the housing.

The housing 23 can be made of a variety of materials and, in one embodiment, the housing 23 is made from plastic. Moreover, the housing 23 can include a cap 25 that can be removably attached to the top end 23a of the housing 23 such as by threaded engagement. Alternatively, the cap 25 may not even be associated with the housing 23. Rather, the cap 25 can be generally associated with the controller 24. For example, the cap 25 can be a cover provided with the controller 24.

The temperature control valve 38 can be any device designed to open, fully or partially, at various temperature levels. In one embodiment, the temperature control valve 38 can simply open fully at a given temperature. In another embodiment, the temperature control valve 38 can begin to open at a first temperature, for example, 40 degrees Fahrenheit. If the temperature continues to drop, the valve 38 can gradually and commensurately open until it fully opens at a second temperature such as 35 degrees Fahrenheit. Alternatively, the temperature control valve 38 can start to open at 35 degrees Fahrenheit and become fully open at 30 degrees Fahrenheit. The settings of the temperature control valve 38 may or may not be adjustable depending on the particular temperature control valve 38.

Naturally, the temperature control valve 38 is configured to measure the water temperature in the first tube 36. Accordingly, the temperature control valve 38 can include, for example, a thermometer or a temperature sensitive metal coil. In one embodiment, the temperature control valve 38 can be a purely mechanical device; in another embodiment, the temperature control valve 38 can have electronic attributes as well.

The first and second tubes 36, 40 of the freeze protection system can have various forms and be made of various materials. For example, the tubes 36,40 can have a variety of cross sections, but generally round is preferred. The tubes 36,40 can be made of metals or plastic. Further, it is preferred if the tubes 36,40 are about ½ inch or, more preferably, about ⅜ inch in diameter. As noted earlier, field testing and operation has demonstrated that tubing 36,40 of such size is less likely to freeze compared to ¼ inch tubing as used in the prior art. The first and second tubes 36,40 can but need not be the same size. Moreover, it should be noted that both the first and second tubes 36,40 can be a single continuous tube or they can comprise multiple tube segments and/or fittings.

With the general arrangement and individual components described in detail, an example of the operation of a freeze protection system according to aspects of the invention will now be described. Initially, the temperature control valve 38 is closed and the first tube 36 is filled with water. The temperature control valve 38 can measure the temperature of the water in or from the first tube 36. The temperature control valve 38 can take measurements on a substantially continuous basis or at any regular or irregular interval. When the water temperature reaches a first temperature, the temperature control valve 38 will begin to open. If the water temperature in the line further cools to a second temperature, the temperature control valve 38 will fully open.

When the temperature control valve 38 opens, water in the first tube 36 can pass through the valve 38. Because of the pressure relief in the first tube 36, the control valve 22 opens to allow water from the water distribution system to flush through the system. Thus, the cold water that was in the system is exchanged for warmer water from the water distribution system. Some of this water will pass through the control valve 22 and into discharge piping 26 as discussed previously. In addition, a portion of the warmer water passes through the t-fitting 34, into the first tube 36 and through the temperature control valve 38.

After passing through the valve 38, the water can flow into a second tube 40. Water in the second tube can be routed to the controller housing 23. As shown in FIG. 3, the second tube 40 enters the housing 23 and coil downwardly around the inner periphery of the housing 23 and ultimately exits the housing 23. At least a portion of the controller 24 is substantially surrounded by the coils of the second tube 40. Thus, as warmer water passes through the coils, the electronic and other components will be warmed. Water exiting the housing 23 will continue to flow through the second tube 40 until it flows into the discharge piping 26 as discussed before. The above flushing operation will continue until the temperature control valve closes such as when it detects a sufficiently elevated temperature. The above operation will repeat itself as necessary. Again, the first and second tubes 36,40 are ⅜ or ½ inches in diameter, which offer protection from freezing between flushing cycles.

In addition to freeze protection, aspects according to the present invention can further relate to providing a device for treating water being flushed from the system. In one aspect, the box-type system can provide apparatus for dechlorinating the discharge water. The dechlorination apparatus can comprise a plurality of components including, for example, a treatment container 80, a treatment substance, and inlet and outlet tubing 86,88. Each of these components will be discussed in order below.

Figure 8:
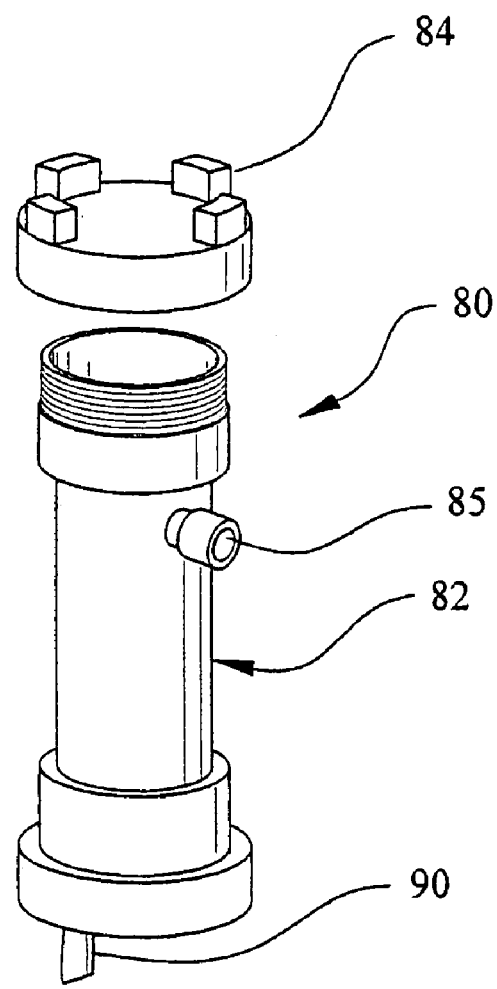
FIG. 8 is an exploded isometric view of a water treatment tower according to aspects of the present invention.

FIG. 8 generally shows an example of a water treatment container 80 for holding a substance for treating discharge water. In one embodiment, the container 80 can generally comprise a generally cylindrical body 82 and a cap 84. The cap 84 and the body 82 can have any of a number of general shapes. For example, instead of being generally cylindrical, the container 80 can be generally triangular, rectangular, polygonal, etc. The cap 84 and the body 82 can be secured by threaded engagement, conforming fit, hinges, fasteners or any other manner such that the cap 84 is removable from the body 82. Alternatively, the cap 84 and body 82 can be secured by welding or adhesives such that the cap is no longer readily removable. In this case, cap 84 can provide an opening or door in which a user can deposit a substance into the interior of the container 80. The housing 80 can be attached to the system using any of a variety of restraints.

The container 80 can be made of any material such as metal or plastic like PVC. Preferably, the container 80 is made from a material that is compatible with the substance intended to be placed inside of the container. In other words, the container 80 will not degrade or otherwise adversely affect the substance contained within and, conversely, the substance will not degrade or otherwise adversely affect the container 80.

The substance to be placed within the container can be any of a number of substances depending on the goal or governmental regulations at issue. For example, if a municipality forbids discharging chlorinated water back into the ground, then the water treatment device can be a dechlorination device and, accordingly, the container 80 can be filled with sodium sulfite in tablet or other form. Alternatively, the housing may contain other substances such as vitamins or minerals for not only treating the water but also the surrounding soil. Further, the container 80 can include one or more different substances. Regardless of the composition of the substance, it is preferred if the substance is provided in solid form such as tablets, granules, pellets or pills, for example. The container 80 can be filled to any level with the substance, and, in one embodiment, the body 82 can include graduated level marking to indicate the level of substance contained inside.

The dechlorination container 80 can be provided with an opening 85 to receive water from an inlet tube 86 (FIG. 1). The inlet tube 86 can be made of various materials such as plastic or metal tubing. The inlet tube 86 can extend from a portion of the discharge piping of the box-system as shown in FIG. 1. The inlet tubing can tie anywhere into the discharge piping. For example, the inlet tubing can tie into a region of the discharge piping 26 where the discharge piping 26 is routing the water downward or it can tie into a region of the discharge piping 26 where the discharge water is flowing generally parallel to the ground surface.

To aid in routing water to the dechlorination tower 80, the discharge piping 26 of the box-system can make use of a reducer 32 for restricting the water flow inside the discharge piping 26. The earlier discussion of the reducer 32 in connection with the vacuum pressure breaker applies equally here as the reducer 32.

When employed, the reducer 32 can increase the pressure in the portion of the discharge piping 26 prior to the reducer 32. The supply line 86 of the dechlorination apparatus can take advantage of this elevated pressure by being connected into the discharge piping 26 upstream of the location of the reducer 42 as shown in FIG. 1. Thus, the supply tubing 86 will provide a path for reducing the pressure build-up. The supply line 86 extends from the discharge piping 26 and into the treatment tower 80. Further, prior to entering the treatment tower 80, the supply line 86 can be fitted with a valve 88 for partially or completely restricting the flow into the tower 80.

The inlet piping 86 can enter the container 80 in a variety of places along the length or circumference of the cylindrical body 82 or through the cap 84. For example, the line 86 can enter at an upper portion of container as shown in FIG. 8. In such case, entering water can percolate down through the dechlorination tablets within the container 80 Alternatively, the line can enter the tower at a relatively low point so that the incoming water washes against the generally lowermost tablets housed within the container 80.

The container 80 can include an opening (not shown) in the bottom 83 of the container 80. In such case, the bottom surface of the container can be inclined so as to facilitate draining of water out of the container through the opening and tubing 90 connected to the opening in the bottom of the container 80. The outlet tubing 90 can ultimately connect back into the discharge piping 26,26*a* of the box-system, preferably in a portion located downstream of the reducer 42. In such case, the relatively low pressure within the discharge piping 26,26*a* in that region can create a suction effect to further facilitate flow of the treated water out of the container 80. The outlet tube 90 can be comprised of various materials such as metals or plastics, and can have any of a number of configurations.

The dechlorinized water exiting the discharge piping 90 can mix with the untreated water being flushed so as to provide a desired average level of dechlorination of the water flushed from the system. The amount of dechlorinization can be controlled in any of a number of ways such as by including more tablets or by providing larger capacity inlet and outlet lines 86,90 or a larger container 80. While the above discussion relates to dechlorination, aspects of the invention are not so limited. For example, the container 80 can house any of a number of substances for treating the water being discharged.

In summary, aspects of the invention relate to various improvements of the box-type water flushing system. Aspects include freeze protection, dechlorination and water treatment and certain backflow features as well.

Like the box-type systems, the column-type systems can have a number of arrangements and can be used in a variety of environments and manners. The column-type systems are especially suited for occasions in which a user wishes to place most, if not all, of the operating components of the system below grade level. Such an arrangement is desirable at least for the reason that it can deter tampering, theft or vandalism.

Figure 9:
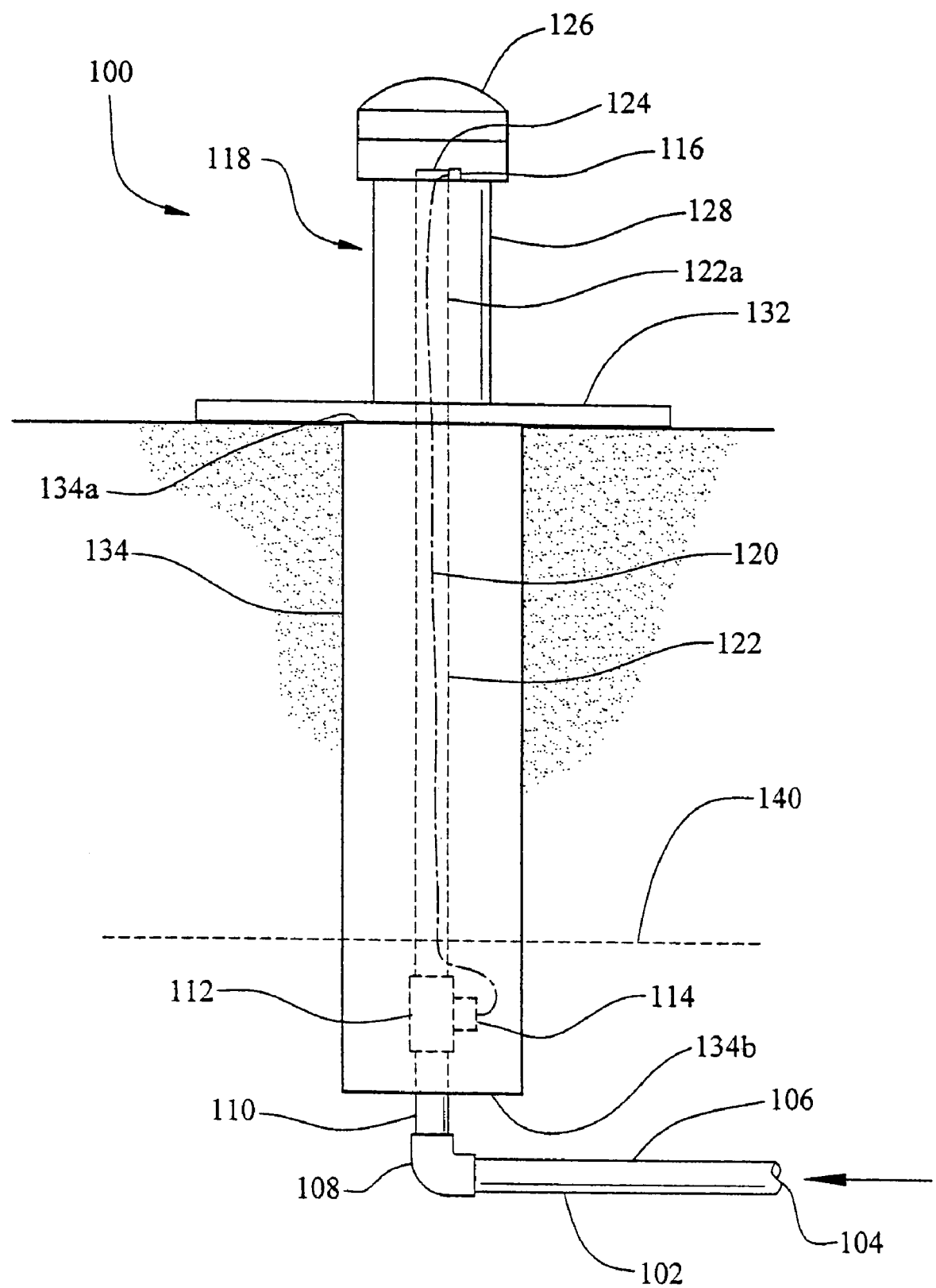
FIG. 9 is a side elevational view of a water flushing system according to aspects of the present invention.
Figure 10:
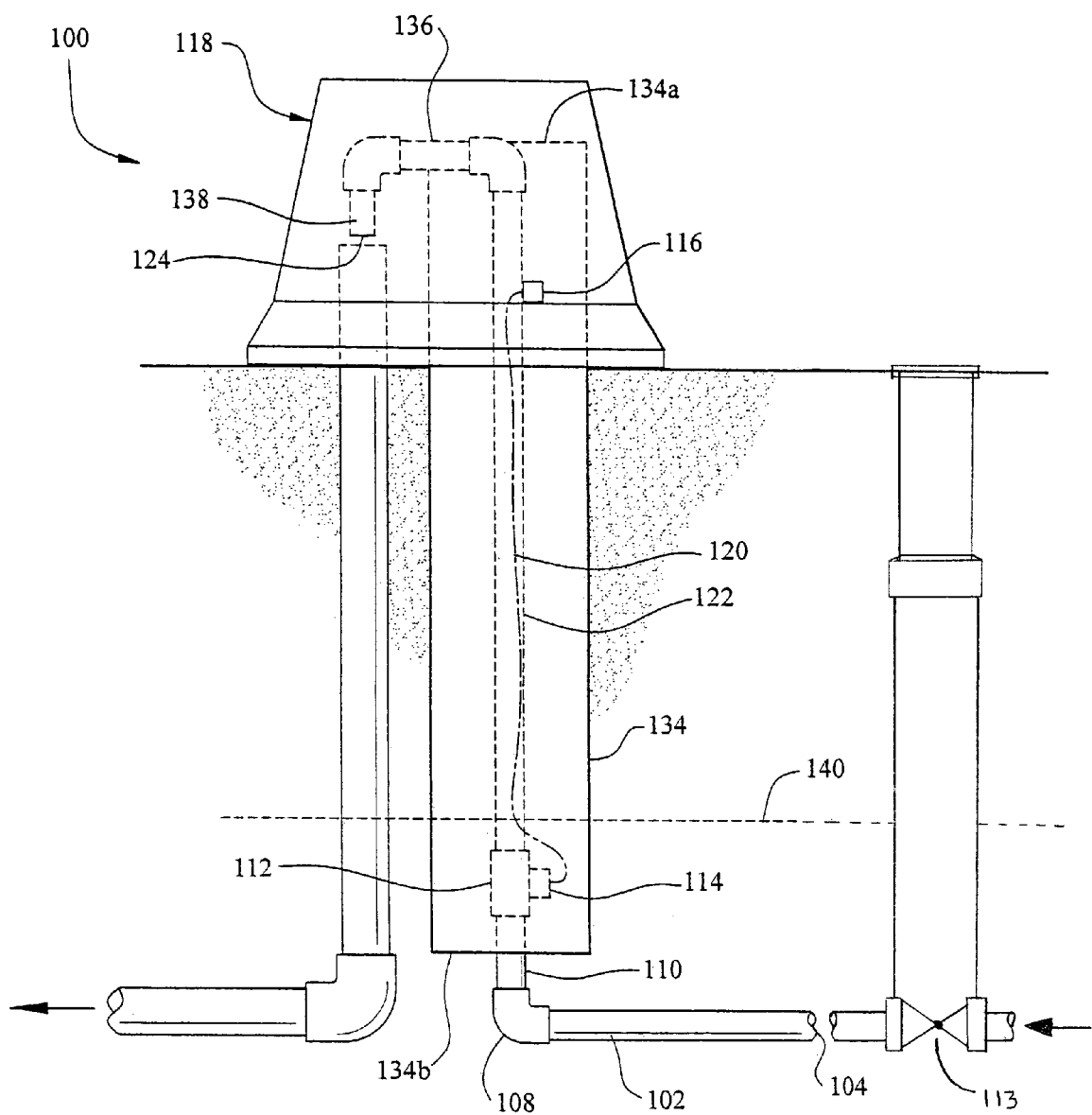
FIG. 10 is a side elevational view of a water flushing system according to aspects of the present invention.

Examples of column-type systems are shown in FIGS. 9-10. A basic column-type system 100 can comprise a plurality of components. The column system can be supplied by a water distribution system (not shown) such as a subterranean pressured water line. Water from the water distribution system can be received in water carrier piping 102 through a water inlet 104. The dimensions and configuration of the water inlet 104 are adapted for connection to the particular piping of the water distribution system. For example, the water inlet 104 can provide a male or a female connector that can include threads.

The water carrier piping 102 can be made up of one or more pipe segments and/or fittings. For example, after connecting to the water distribution system, the water carrier piping can include pipe fittings such as an elbow, tee or other fitting so as to change the direction of the incoming water. In one case, the water distribution system may be oriented generally horizontally. In such case, the water carrier piping can include a generally horizontal pipe segment 106 for connection to the water distribution system. The other end of the water carrier piping segment 106 can connect to a 90 degree elbow 108. Another pipe segment 110 can extend generally vertically upward from the other end of the elbow 108. Generally vertical means true vertical as well as deviations therefrom. Thus, the incoming water enters the water carrier piping 102 in a generally horizontal manner and is redirected through the water carrier piping 102 to become generally vertical. Instead of having multiple pipe segments 106, 108, 110, the water carrier piping 102 can be a single piece shaped so as to have the desired path.

Regardless of the exact configuration, the water carrier piping 102 can generally be connected at one of its ends to the water distribution system and at its other end to other components of the water flushing system 100. The water inlet piping 102 can be connected to the other components of the water flushing system 100 in various manners such as by threaded engagement, adhesives, fasteners or welding. Preferably, the water flushing system 100 and the water carrier piping 102 are detachably connected together by a quick connect/disconnect device.

A quick connect/disconnect device can be a detachable coupling set such as a cam lock, which is known in the art. A cam lock device is illustrated in FIGS. 27-30. In general, a cam lock can comprise a male connector portion and a female receptacles portion. The cam lock can provide one or more rotatble cam members, which can be integral with a user handle for rotating the cam members. Additional aspects of the cam lock system will be described in greater detail below.

Again, the water carrier piping and the water distribution system can be detachably connected. Accordingly, one end of the water carrier piping can include a cam lock-fitting such as a male connector portion. Naturally, the mating component of the column-type water distribution system can be provided with a corresponding cam lock fitting such as a female receptacle portion.

In one water flushing system, water can flow from the water carrier piping 102, through the cam lock and into a flow controlled passage 110 of the column-type system. Water entering the flow controlled passage 110 encounters a flow control valve 112. The valve 112 can control the rate at which water is purged from the system. When not in a flushing mode, the valve 112 can completely restrict the flow of the incoming water from the main line. The valve 112 can be any type of valve such as a ball valve. Preferably, the valve 112 is capable of passing sand and other debris without obstructing the valve 112. The control valve 112 can be constructed of various materials including metals and plastics such as non-corrosive glass reinforced nylon.

A programmable controller 114 can be provided for activating and deactivating the flow control valve 112. Thus, the controller 114 can be programmed to activate the flow control valve 112 in various settings or cycles. For example, the controller 114 can be set for a specific day, at a desired time of day and/or for a specified duration of time. In one embodiment, the controller 114 can be integrated with the flow control valve 112. The programmable controller 114 can be a solenoid controller. Preferably, the controller 114 can be powered by a power supply such as a replaceable self-contained power sources like a 9-volt battery. Ideally, the power source can have an operating life of about 8 months to 12 months under normal operating conditions.

The controller 114 can store instructions from hand-held detachable programmer (not shown). The programmer can transmit instructions to the controller in numerous ways. In one embodiment, the column-type system can provide a programming/data retrieval port 116, such as a standard telephone handset jack, which can be integrated into a portion of the apparatus housing 118. Preferably, the port 116 is waterproof. As shown in FIGS. 9 and 10, the port 116 can generally be located in several places. When the port 116 and controller 114 are separated, a cord 120 can be provided to connect between the port 116 and the controller 114.

The port 116 can be adapted for receiving instructions from a remote hand-held programming device (not shown). For instance, the hand-held programming device can comprise a lap-top computer. The hand-held electronic device can communicate programming instructions to the programmable controller 114 in sundry manners. The port can provide for either uni-directional or bi-directional communication between the programming device and the controller 114.

After the flow control valve 112, the system includes substantially straight and generally vertical piping 122, which may comprise a single pipe or a plurality of pipes and/or fittings. The vertical piping 122 can connect into the flow control valve 114 in sundry manners such as by threaded engagement, adhesives, fasteners or any combination thereof. The vertical piping 122 can be made of any material but plastics such as PVC are preferred.

Once the water passes through the vertical piping 122, it can be discharged from the water flushing system 100. Preferably, at least a portion of the vertical piping 122 and its discharge end 124 extend above grade level. There are an assortment of ways to discharge the water from the column-type system. In one system, shown in FIG. 9, the water flows vertically upward until it impinges on a cap 126, which redirects the water downward toward the ground. To aid in discussion, this configuration will be referred to as the "cap-redirect" system.

Figure 11:
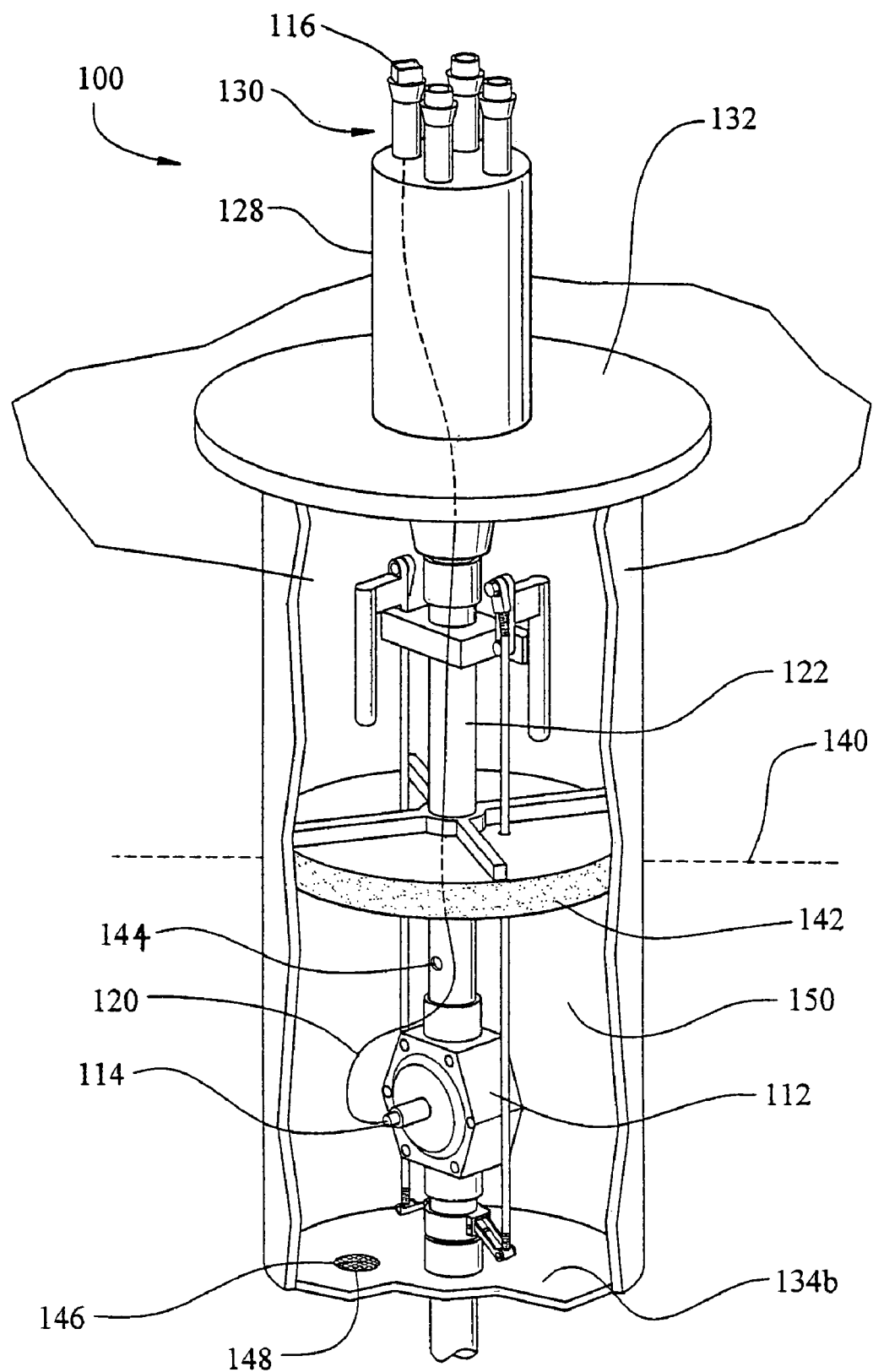
FIG. 11 is an isometric view of a water flushing system according to aspects of the present invention.

In the cap redirect system, the portion of the vertical piping that extends above grade level 122a can be enclosed within a housing. The housing can have any conformation so long as it provides protection from the outer environment. Preferably, the housing includes a generally cylindrical body portion 128 and a cap portion 126. As shown in FIG. 11, a portion of the generally cylindrical body portion 128 can include a mount 130 for the port 116.

With respect to the cap-redirect configuration, a splash guard 132 can be provided about the base of the housing 128 so as to prevent erosion of the soil surrounding the unit as a result of repeated direct discharge. The splash guard 132 can have any shape such as being generally circular. Further, the splash guard 132 can be made of a variety of materials like plastics or metals including aluminum. The splash guard 132 can be secured in place in any of a number of ways. For example, the splash guard 132 can include provisions for mounting into the ground itself and/or the above-ground 128 or below-ground 132 housings.

FIG. 10 shows another discharge configuration, which shall be referred to as the "pipe-redirect" system. In the pipe-redirect system, the water can be routed vertically up and redirected downward through one or more discharge pipes (122, 136, 138). The discharge pipes can be a single pipe or a plurality of pipes and/or fitting to redirect the water downward. In addition, the discharge pipes can be an extension of the generally vertical piping 122. In any event, the water is discharged downwardly and into a below grade location such as a storm drain, sewer line or drain field. The above ground components of the "pipe redirect" system can be enclosed within a housing 118.

The column system can extend below ground to a variety of depths such as from about 3 feet to about 9 feet or from about 5 feet to about 7 feet. The underground portion of the system can be contained within a housing 134. The housing can have various conformation such as cylindrical as shown in FIGS. 9 and 10. However, the housing can also be square, triangular, polygonal, rectangular, oval, or irregular in cross-section. The housing 134 can have any conformation so long as it generally shields the system from the surrounding earth. The top 134a and bottom 134b ends of the housing can be open or closed. Preferably, the bottom end 134b is closed. However, any openings provided in the bottom 134b of the housing 134 for permitting component to pass through can include material such as a gasket to substantially seal the bottom from the infiltration of water and soil.

When buried at least partially underground, the column-type systems can make use of a natural freeze protection phenomenon to ensure that its components do not freeze. In particular, there is a certain depth, which varies from place to place, below which the ground does not freeze. This depth is known as the freeze or frost line. Because the ground below the frost line does not freeze, it follows that any components of the water flushing system disposed below the frost line will not freeze.

Thus, in one embodiment, the main operating components of the column-type system such as the control valve 112 and controller 114 can be disposed below the frost line 140. Moreover, insulation material 142 such as foam can be provided inside of the housing 134 so as to separate the components above and below the frost line 140. In such case, the insulation material 142 is disposed substantially at the frost line 140.

Thus, the insulation 142 retains the warmth below the frost line 140 while impeding the infiltration of freezing temperatures of the earth above the frost line 140. Naturally, the depth at which the frost line 140 lies can vary from place to place.

Having described the basic components, assembly and operation of two types of column-style systems, aspects of the present invention pertaining to these systems shall now be described.

Aspects of the present invention relate to freeze protection and backflow prevention. As noted above, the column-type systems 100 can provide one form of freeze protection by placing the functioning components of the system below the frost line to ensure that those components will not freeze. Despite this protection, the system may nevertheless be exposed to dangers associated with freezing temperatures such as component damage due to the expansion of freezing water. For example, after completing a flushing operation, water may remain in the generally vertical piping 122 of the system. At least for the portion of the vertical piping 122 that extends above the frost line 140, the retained water can eventually freeze before the next purging cycle occurs, causing piping or other components to break or rendering the system inoperative by blocking fluid flow.

Therefore, aspects of the present invention relate to a way for draining the water from the vertical column 122 at least to a level below the frost line 140. Accordingly, in one aspect, a column-type system according to aspects of the present invention can include a weep hole 144 in the vertical piping so as to allow water to drain out of the vertical piping 122. Such a system is shown in FIG. 11.

The weep hole 144 can be located anywhere along the length and circumference of the vertical piping 122 so long as it is below the frost line 140 yet after the control valve 112. The weep hole 144 can have any of a number of conformations such as round, circular, oval, oblong, circular, rectangular, polygonal, or irregular, just to name a few. The weep hope 144 can be any of a variety of sizes. Further, the weep hole 144 can extend through the thickness of the vertical piping 122 at any angle with respect the outer surface of the vertical piping 122. The weep hole 144 can be added to the piping 122 in any of a variety of manners including, for example, by cutting, drilling or punching.

When a weep hole 144 is provided, the system can include a drain hole 146 in a bottom surface of the housing 134b to permit water to flow out of the unit and into the surrounding soil. The drain hole 146 can be covered with a wire mesh 148 or cloth or other material so as to prevent debris or other material in the surrounding soil from entering the housing. The drain hole 146 can be any of a variety of sizes and can be sized to provide a desired flow rate. Further, the drain hole 146 can be disposed anywhere on the bottom surface of the housing 134b. In one embodiment, at least a portion of the bottom surface of the housing 134b can be generally sloped toward the drain hole 146 so as to guide water discharged from the weep hole 144 to the drain 146.

A column-type system 100 having a weep hole 144 can operate as follows. After a flushing operation, water can remain in the vertical piping column 122. However, the weep hole 144 provides an exit path through the water can flow out of the vertical piping 122. Water exiting the weep hole 144 will flow into the interior of the housing such as an interior compartment 150 defined between the insulation 142 and the bottom of the housing 134b. The water will continue to flow through the weep hole 144 until the water level in the column 122 is at or below the level of the weep hole 144. At that point, any remaining water will be below the frost line 140 and the dangers of freezing will be eliminated.

The water that has poured into the interior of the housing 150 can exit the system through the drain hole 146. It should be noted that not only does the weep hole 144 permit water to exit the vertical piping 122 after a flushing operation, but it also allows water to flow from the weep hole 144 during a flushing operation. During a flushing mode, most of the water is routed vertically upward through the vertical piping 122 and ultimately discharged from the system in any of the manners previously discussed. However, a portion of the water can flow out through the weep hole 144 and into the sub-frost line compartment 150 of the housing 134. Again, this water can flow out of the housing 134 through the drain hole 146.

While the weep hole 144 can remedy the concern of residual water in the vertical piping 122, it may sometimes be undesirable to have water flowing out of the weep hole 144 during the flushing cycle of the system. For example, it may not be desirable to drain excessive amounts of water to the soil surrounding the system due to soil saturation and/or erosion. Also, the additional water can make the compartment 150 unnecessarily wet and/or dirty. Accordingly, aspects of the invention further relate to provisions for allowing water to drain from the vertical column 122 only when the system is not in a flushing mode. In other words, aspects of the invention relate to provisions for preventing water from flowing out of the column 122 and into the sub-frost line compartment 150 during a flushing operation.

Figure 12:
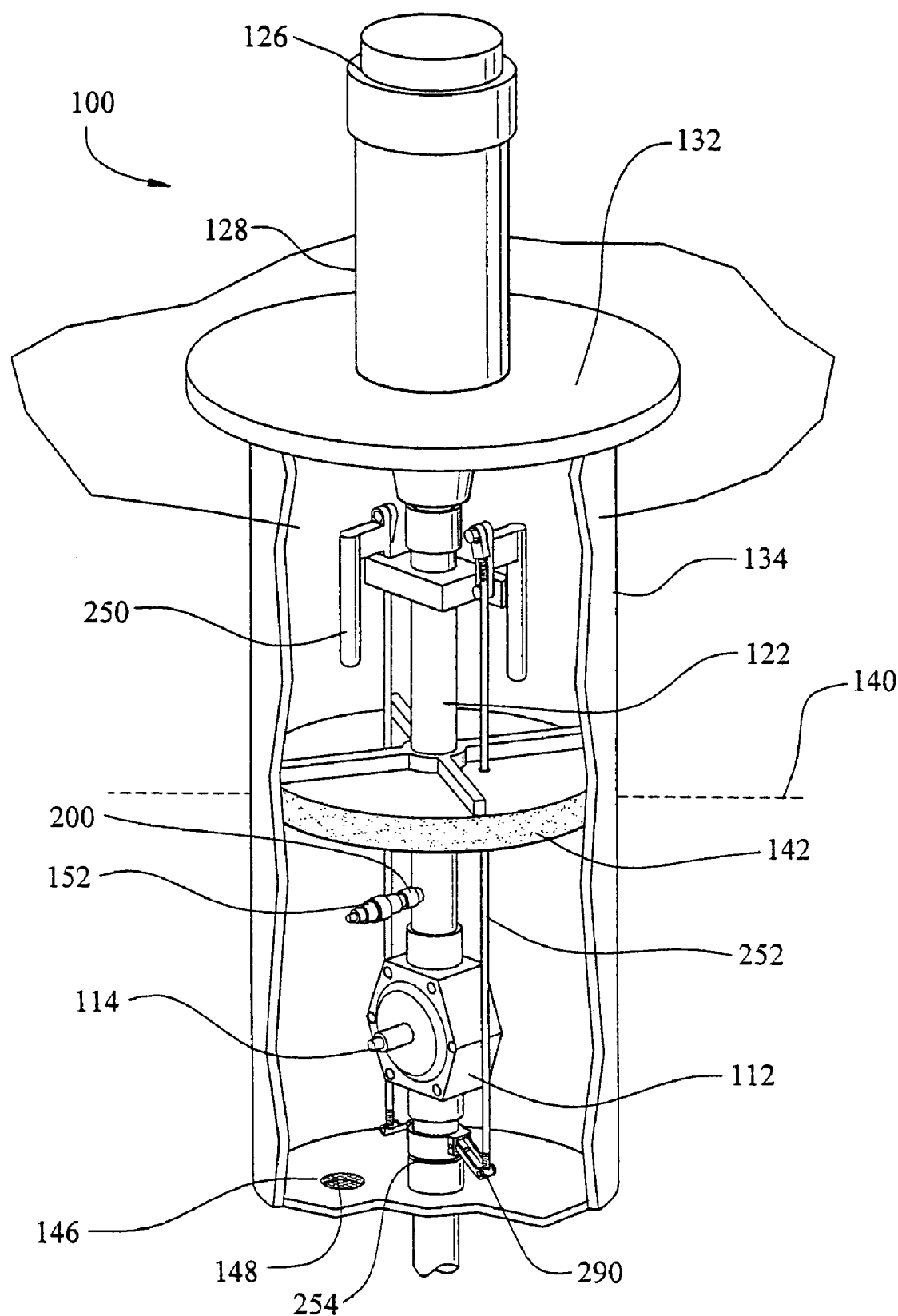
FIG. 12 is an isometric view of a water flushing system according to aspects of the present invention.

The desired results can be achieved in a variety of ways in accordance with aspects of the present invention. In one embodiment, the present invention can provider one or more valves or fittings, either in combination or individually, that can effectuate the desired results. For example, as shown in FIG. 12, the present invention can include a combination of a relief valve 152 and a pressure increase fitting 200. Each of these components will be discussed in detail below.

Figure 16:
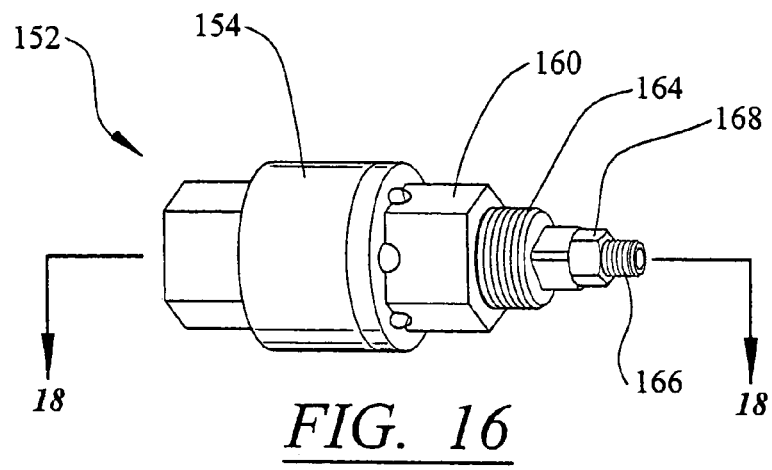
FIG. 16 is an isometric view of a valve according to aspects of the present invention.
Figure 17:
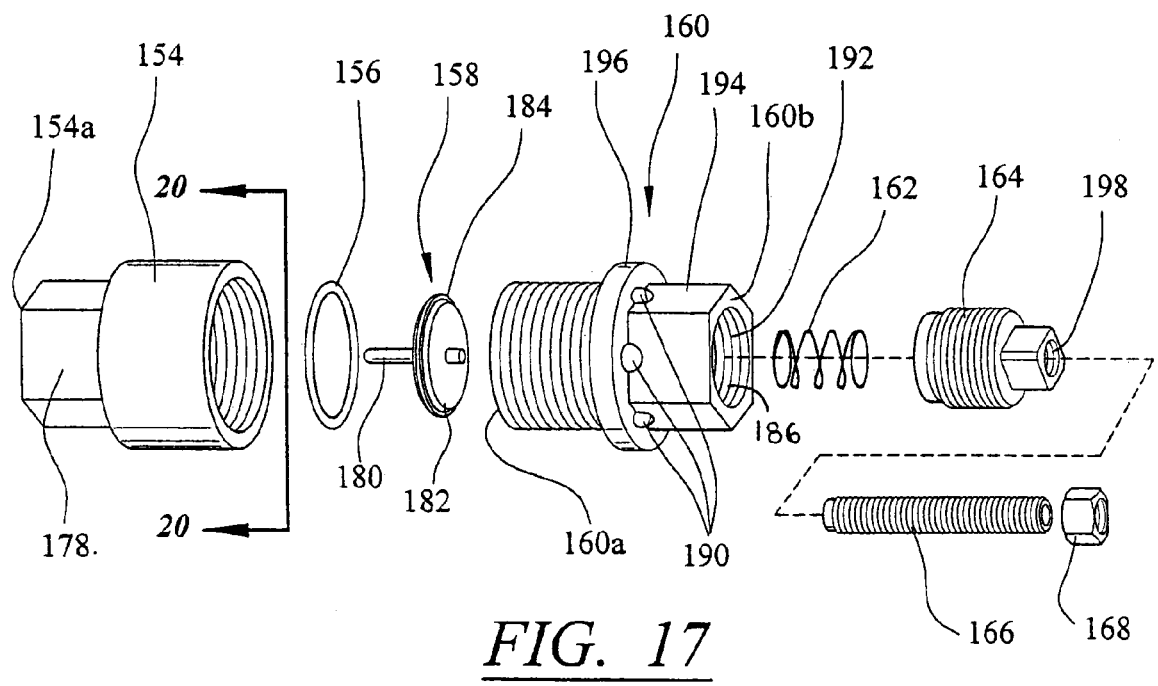
FIG. 17 is an exploded isometric view of a valve according to aspects of the present invention.

The relief valve 152 can be any component that blocks the flow of pressurized fluid through the valve while permitting low or non-pressurized flow to freely pass through the valve. One example of such a low pressure relief valve 152 is shown in FIG. 16. The relief valve 152 can comprise a multitude of individual components. As shown in FIG. 17, a low pressure relief valve 152 can comprise a first shell 154, an o-ring 156, a plunger 158, a second shell 160, a biasing member 162, a coupling 164, an elongated member 166 and a closing member 168. Each of these components will be discussed in turn below.

The first shell 154 can have any of a variety of forms. In one embodiment, the first shell 154 can have female receptacles at each end. Each female receptacle can be provided with internal threads for threadably engaging with other components. The female receptacles can be identical and, in such case, can comprise one substantially continuous threaded axial passage through the first shell. However, the end configurations need not be identical or even similar. For example, one end can provide a male connection and the other a female receptacle.

Figure 18:
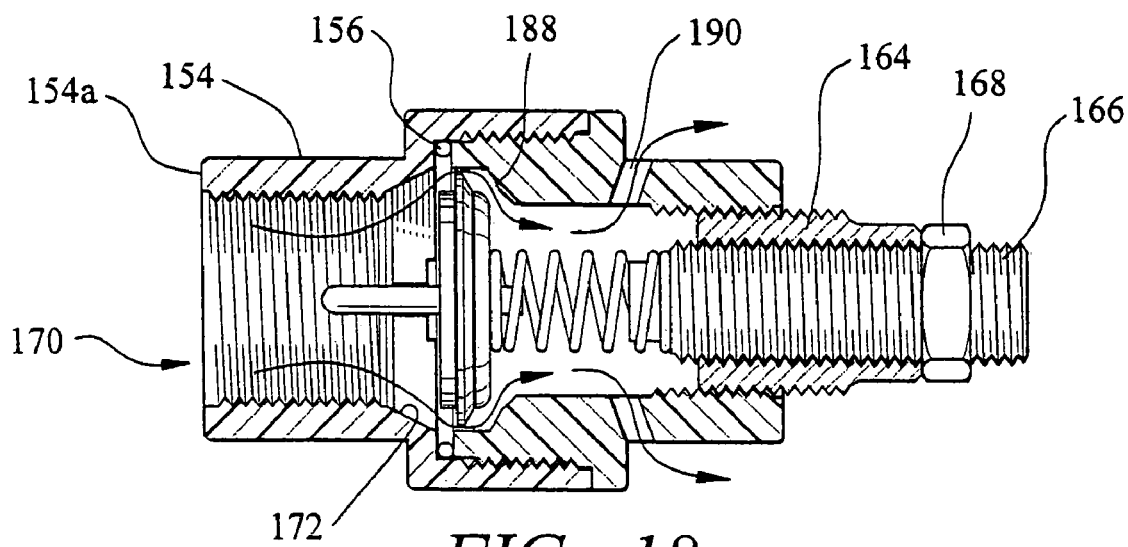
FIG. 18 is a cross-sectional view of a valve according to aspects of the present invention, taken along line 18-18 of FIG. 16.
Figure 20:
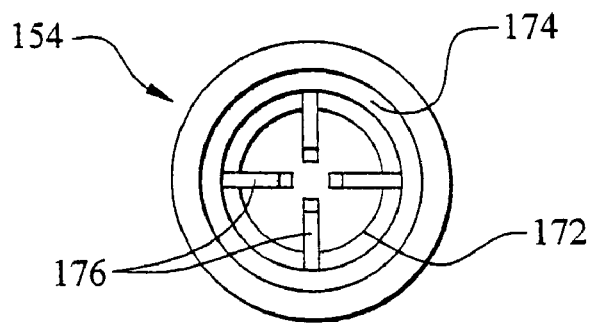
FIG. 20 is a side view of a first shell member of the valve according to aspects of the present invention, viewed along line 20-20 of FIG. 17.

In the example shown in FIGS. 17, 18 and 20, the first shell includes threaded female receptacles at each end 154a, 154b with the receptacles being of unequal size. The receptacles define part of an inner axial passage 170 extending through the first shell 154. In addition, the inner axial passage 170 includes an unthreaded region 172 between the first and second receptacles 154a, 154b; this unthreaded region 172 can be tapered or it may be generally straight. Further, the first shell 154 can provide a shelf portion 174 that extends substantially about an inner periphery of the first shell. The shelf 174 can be any width and is preferably sized so as to accommodate the o-ring or gasket material 156.

One or more positioning members 176 can be provided within the inner axial passage 170 of the first shell 154. For example, the position members 176 can include a plurality of inwardly extending arms. The positioning members 176 can have any of a variety of configurations so long as they can generally position the plunger 158, maintain the plunger 158 in position, and do not substantially restrict fluid flow through the inner axial passage 170. The positioning members 176 can be positioned anywhere in the first shell 154 and, in one embodiment, four positioning members 176 are located in the unthreaded region 172 of the inner axial passage 170 and project radially inward therefrom.

The outer surface of the first shell can have miscellaneous conformations. Preferably, at least portion of the outer surface of the first shell can include a hexagonal surface 178 for allowing a user to engage a tool such as pliers or a crescent or adjustable wrench to tighten or loosen the first shell as may be necessary. The first shell 154 can be made of any of a variety of materials including metals or plastics. In one embodiment, the first shell 154 is a molded plastic piece.

The plunger 158 of the valve 152 according to the invention can generally include a flange portion 182 and a shaft portion 180 extending outward from one side of the flange portion 182. In one embodiment, the shaft portion 180 can extend substantially perpendicular to the flange 182. Substantially perpendicular can include true perpendicular and deviations therefrom. The flange portion 182 and the shaft portion 180 can be a unitary piece or separate pieces joined in any of a variety of manners. The flange portion 182 can be any shape and is preferably generally circular. The flange portion 182 can further include compressible material 184 such as a gasket for sealingly interfacing with another surface. In one embodiment, the flange portion 182 includes two generally disk-like pieces with compressible material sandwiched therebetween.

The next component that can be part of the valve assembly is a second shell 160. In one embodiment, the second shell 160 includes a threaded male connector at one end 160*a* and a threaded female connector at the other end 160*b*. The male connector end 160*a* can be sized and have associated features so as to be matingly received in one of the female ends 154*b* of the first shell 154.

The second shell 160 can include an axial passage 186 extending at least partially through its interior. The axial passage 186 can include a surface 188 for substantially sealingly engaging with the flange portion 182 of the plunger 158. The flange engaging surface 188 can be sloped or generally straight. Subsequent to the flange engaging surface 188, the axial passage 186 includes one or more outlet holes 190 that extend through the second shell 160. The outlet holes 190 can be arranged circumferentially about the second shell 160 and, in one embodiment, six outlet holes 190 are so arranged. The outlet holes 190 can be any size, shape and at any orientation with respect to the axial passage 186. Preferably, the holes 190 are generally circular in cross-section.

The other end of the second shell 160*b* can be configured in several ways. For example, it can be closed so as to eliminate the need for the elongated member 166, the closing member 168 and the coupling member 164. In another embodiment, this end of the second shell 160 can include a threaded opening 192 for receiving the coupling member 164.

As for its outer surfaces, the second shell 160 can be contoured in various ways and include a number of features. For example, at least portion of the outer surface of the second shell 160 can include a hexagonal surface 194 for allowing a user to engage a tool such as pliers or a crescent or adjustable wrench to tighten or loosen the first shell as necessary. In addition, the second shell 160 can include a flange portion 196 between the hexagonal portion 194 and the threaded male end 160*a*. The second shell 160 can be made of any of a variety of materials including metals or plastics. In one embodiment, the second shell 160 is a molded plastic piece.

The biasing member 162 can be, for example, a spring. Further, the biasing member 162 can have any amount of resilience. The biasing member 162 can be anything so long as it can provide a biasing force against the flange portion 182 of the plunger 158. The biasing member 162 can be made of any material, preferably one that does not rust or degrade upon exposure to water.

The elongated member 166 can be any of a variety of things such as a bolt or a threaded rod. The elongated member 166 can be made of any of a variety of materials, but metals such as stainless steels are preferred.

The coupling member 164 serves as a connection between the elongated member 166 and the second shell 160. In one embodiment, the coupling 164 and the elongated member 166 can be a single piece. The coupling 164 can have an opening 198 to accommodate the elongated member 166. For example, when the elongated member 166 is a threaded rod, the opening 198 of the coupling 164 can include internal threads for threadably engaging the elongated member 166. Preferably, when assembled, a portion of the elongated member 166 extends from both ends of the coupling member. One end, the extending portion of the elongated member 166 can be used to position the biasing member 162; the other extending end of the elongated member 166 can be used to engage with the closing member 168.

Further, the coupling 164 can be configured so as to matingly be received in or matingly engage with the second shell 160. For example, when one end 160*b* of the second shell 160 provides a threaded female end, the coupling 164 can provide a threaded male end so as to matingly engage the second shell 160. The coupling member 164 can be made of many materials like metals or plastics, especially those that do not corrode or degrade, in water. In one embodiment the coupling 164 and the elongated member 166 can be a single part.

The closing member 168 can be any device used to retain the elongated member 166 in position with the coupling member 164. For example, it could be any mechanical fastener such as a nut. Alternatively, the closing member 168 can be glue or other adhesive.

Having described the individual components that can comprise the relief valve 152, one manner in which these components can be assembled will now be described. The elongated member 166 can be threaded into the coupling member 164 so that a portion of the elongated member 166 extends through each axial end of the coupling 164. Next, the coupling 164 can be screwed into one end of the second shell 160 so as to substantially sealingly close that end of the second shell 160.

The spring 162 can then be placed inside the second shell 160 proximate to the protruding portion of the elongated member 166 and/or the end of the coupling member 164. For example, the spring 162 can be placed over the protruding end of the elongated member 166.

Next, the plunger 158 is placed inside of the first shell 154 such that the shaft portion 180 of the plunger 158 is generally positioned between the positioning members 176. In such case, the one side of the flange portion 182 of the plunger 158 can be proximate to the positioning members 176. An o-ring 156 can then be placed in the first shell 154 such that it rest on or is substantially adjacent to the ledge portion 174 of the first shell 154.

The first and second shells 154,160 can be secured together by threaded engagement. When assembled, the flange portion 196 of the second shell 160 can be substantially proximate to one end 154b of the first shell 154. Further, when assembled, the o-ring 156 can be compressed between the ledge 174 and the end of the second member 160a. Furthermore, the spring 162 can be substantially proximate to the flange portion 182 of the plunger such that the spring 162 exerts a spring force on the plunger 158. Finally, a nut 168 can be added to close the system.

Once assembled, the resistance of the spring 162 can be adjusted by tightening the coupling member 164 and/or elongated member 166 so that either of these members extends further in or out of the second shell 160. In other words, the more the coupling 164 is tightened, the more the coupling 164 extends into the second shell 160 to thereby increase the force exerted by the spring 162 against the plunger 158. Alternatively, when the coupling 164 is loosened, the coupling 164 does not extend as far into the second shell 160 and, therefore, the spring 182 will exert a lesser force against the plunger 158.

Figure 19:
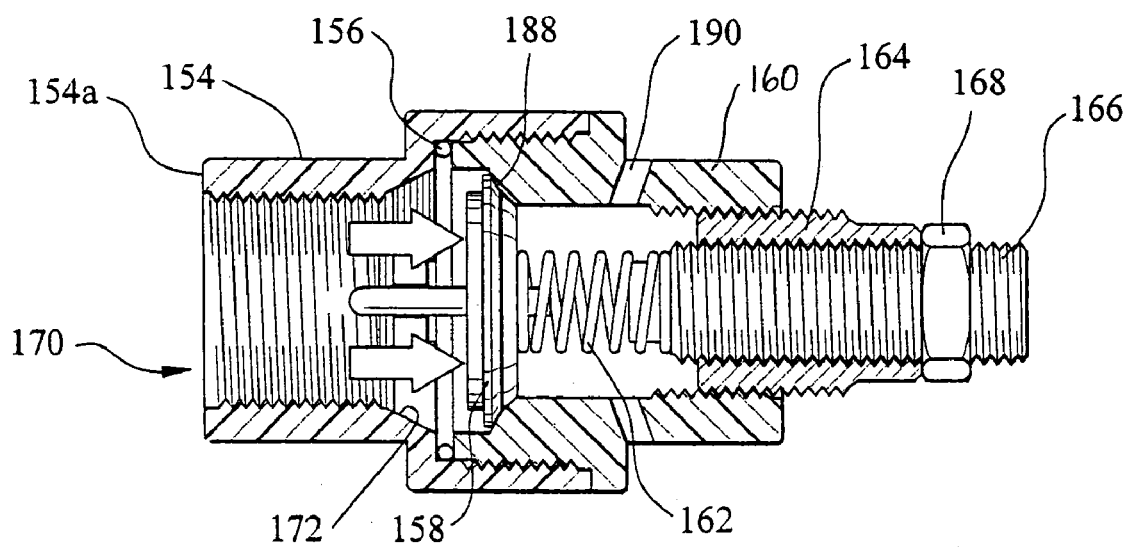
FIG. 19 is a cross-sectional view of a valve according to aspects of the present invention while under pressure.

The relief valve 152 can be used by itself such as by connecting it directly into the generally vertical piping 122 through, for example, the weep hole 144 or other opening below the frost line 140. In such case, the first shell 154 can be provided with a threaded male connection end so that it can be screwed into the vertical piping 122. In operation, water will initially flow into the valve 152 from the first shell end 154. If the water is pressurized, such as water being purged from the system during a flushing mode, it can push the plunger 184 into substantially sealing engagement with a sealing surface 188 of the second shell 160 as is shown in FIG. 19. Thus, the pressurized water will not be able to pass through the valve. However, while the plunger 158 is depressed, the spring 162 is urging the plunger 158 out of engagement with the surface 188 of the second shell 160. As shown in FIG. 18, once the water pressure ceases or diminishes to be less than the spring force, the spring 162 will unseat the plunger 158 from its substantially sealing engagement with the surface 188 so as to allow water to pass around the plunger 158 and out through the outlet holes 190 in the second shell 160.

Further, the relief valve 152 can be indirectly connected into the generally vertical piping 122. Any fitting can be used for this purpose and, in one embodiment, aspects of the invention can provide a fitting for increasing or maintaining a level of pressure on the plunger 158 so as to effectuate substantial sealing engagement with the second shell 160.

One example of a pressure increase fitting 200 according to aspects of the present invention is shown in FIGS. 21-24. The fitting 200 is a generally cylindrical component having a first end 202 and a second end 204. In the embodiment shown, each of the first and second ends comprise male connections with external threads. These are merely examples of possible configurations for the ends as the ends can also be female connections possibly having internal threads as well. The ends 202, 204 of the fitting can but need not be identical or even similar.

There can be an engaging surface 206 between the two ends for, allowing a tool to be connected. The engaging surface 206 can be, for example, a hexagonal surface for interfacing with a wrench or pliers. Other configurations are possible for the surface 206 and, in one embodiment, there may not be an engaging surface 206 at all; instead, the exterior of the fitting can be threaded along its entire length.

An opening 208 extends axially through between the two ends 202, 204 of the fitting 200 for permitting the flow of a fluid such as water. The axial opening 208 can be generally cylindrical but can have any of a number of shapes.

The fitting 200 can further include a partial nipple 210 at one of its ends. The partial-nipple 210 can be generally semi-cylindrical or any other configuration so long as it does not extend completely around the end 204 of the fitting 200. Other nipple 210 cross-sectional configurations include rectangular, semi-oval, and semi-polygonal, to name a few. Preferably, the partial-nipple 210 is only at one end of the fitting.

The pressure increase fitting 200 can be made of any of a variety of materials such as plastics or metals like stainless steel, brass or aluminum. The fitting 200 can be made in any manner in which conventional fittings and fasteners are made such a being machined. While it is preferred if the fitting 200 is a single piece, it is possible for the fitting 200 to be made from more than one piece.

Having described the details and/or assembly of the pressure increase fitting 200 and low pressure relief valve 152, one manner in which such devices can be used together in connection with a column-type system 100 will now be described. The pressure increase fitting 200 can be inserted into the vertical piping 122 of the column-type system 100. For example, the nipple-end 210 of the fitting 200 can be inserted into the weep hole 144 or other opening in the vertical piping 122 below the frost line 140. Next, the first shell 154 end of the relief valve 152 can be attached to the other end of the fitting 200. Preferably, the fitting 200 is inserted into the vertical piping 122 so that the partial-nipple 210 is on the top as generally shown in FIG. 22. In other words, the fitting 200 is ideally positioned so that the open face 212 of the partial-nipple 210 faces the oncoming flow. Thus, when pressurized water flows through the vertical piping 122 during a flushing operation, the partial-nipple 210 of the fitting 200 acts as a scoop so as to route some of the oncoming flow through the fitting 200 and to the valve 152. The partial-nipple 210 can capture a portion of the dynamic head of the flushing water. Moreover, field experience has demonstrated that this orientation can ultimately increase the pressure applied to the plunger 158 so as to provide improved sealing with the second shell 160.

The combination of the relief valve 152 and the fitting 200 can preclude water from flowing into the interior of the housing 150 while the system is flushing. However, still further improvements can be made to the system 100 because experience has shown that dirty or contaminated water can, in certain circumstances, be suctioned back into the system through the relief valve 152. The water being sucked back in can be the water generally standing in the interior of the compartment 150 waiting to drain. This water can contain contaminants or may become contaminated or dirtied while standing in the housing. Thus it is desirable if this water is not allowed to enter the water supply. However, this can be problematic since the basic vertical system 100 does not include backflow prevention at that point in the apparatus.

Thus, aspects of the present invention further to preventing the possibility of backflow through the relief valve 152. Accordingly a check valve 214 can be added between the fitting 200 and the relief valve 152. The check valve 214 can be any valve that generally only permits unidirectional flow through the valve. The check valve 214 can be any type of valve; ideally, the check valve is a double check valve, preferably of the in-line type.

Figure 13:
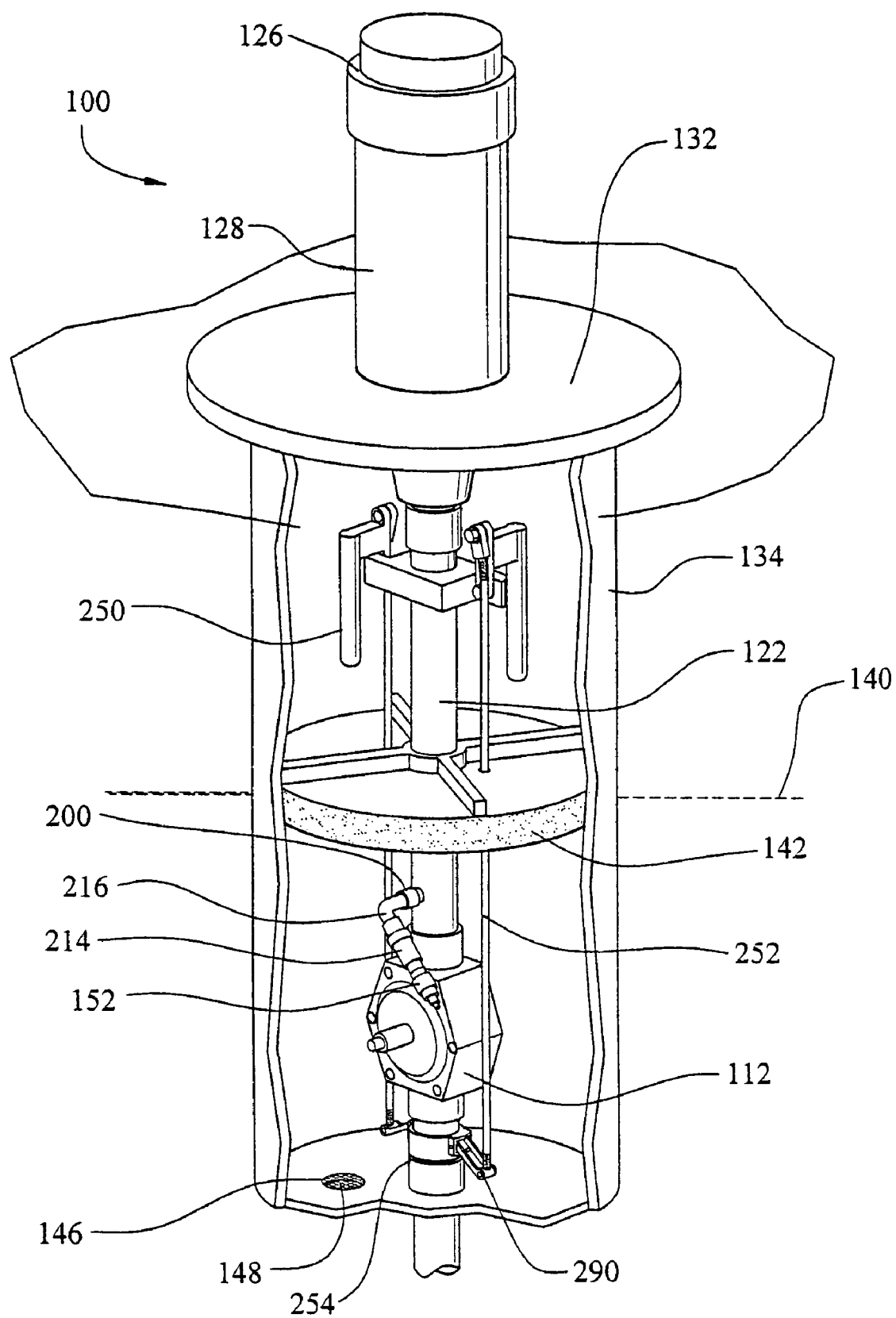
FIG. 13 is an isometric view of a water flushing system according to aspects of the present invention.

One embodiment of a column-type water flushing system including a double check valve 214 is shown in FIG. 13. In this arrangement, the fitting 200 can be inserted into the vertical piping in any of the manners previously described. The other end of the fitting can now connect into the double check valve 214. To avoid the string of valves and fittings from becoming too long in one direction and possibly interfering with neighboring components, one or more fittings such as an elbow 216 can be interposed between the pressure increase fitting 200 and the check valve 214. The other end of the check valve 214 can be connected to the relief valve 152.

The above-described assembly generally operates as previously described. But now the double check valve 214 will prevent contaminated or dirty water sucked in through the relief valve 152 from contaminating the supply water.

However, during field operation and testing, the double check valve 214 and/or the relief valve 152 occasionally locked up and prevented flow out of the column so as to expose a system to the dangers of freezing conditions. The lock-up may have been caused by a pressure buildup in the passage between the double check valve 214 and the relief valve 152. Thus, aspects of the present invention are directed to preventing lock up of the check valve 214 and/or the relief valve 152 by providing a pressure release between the two valves.

Figure 14:
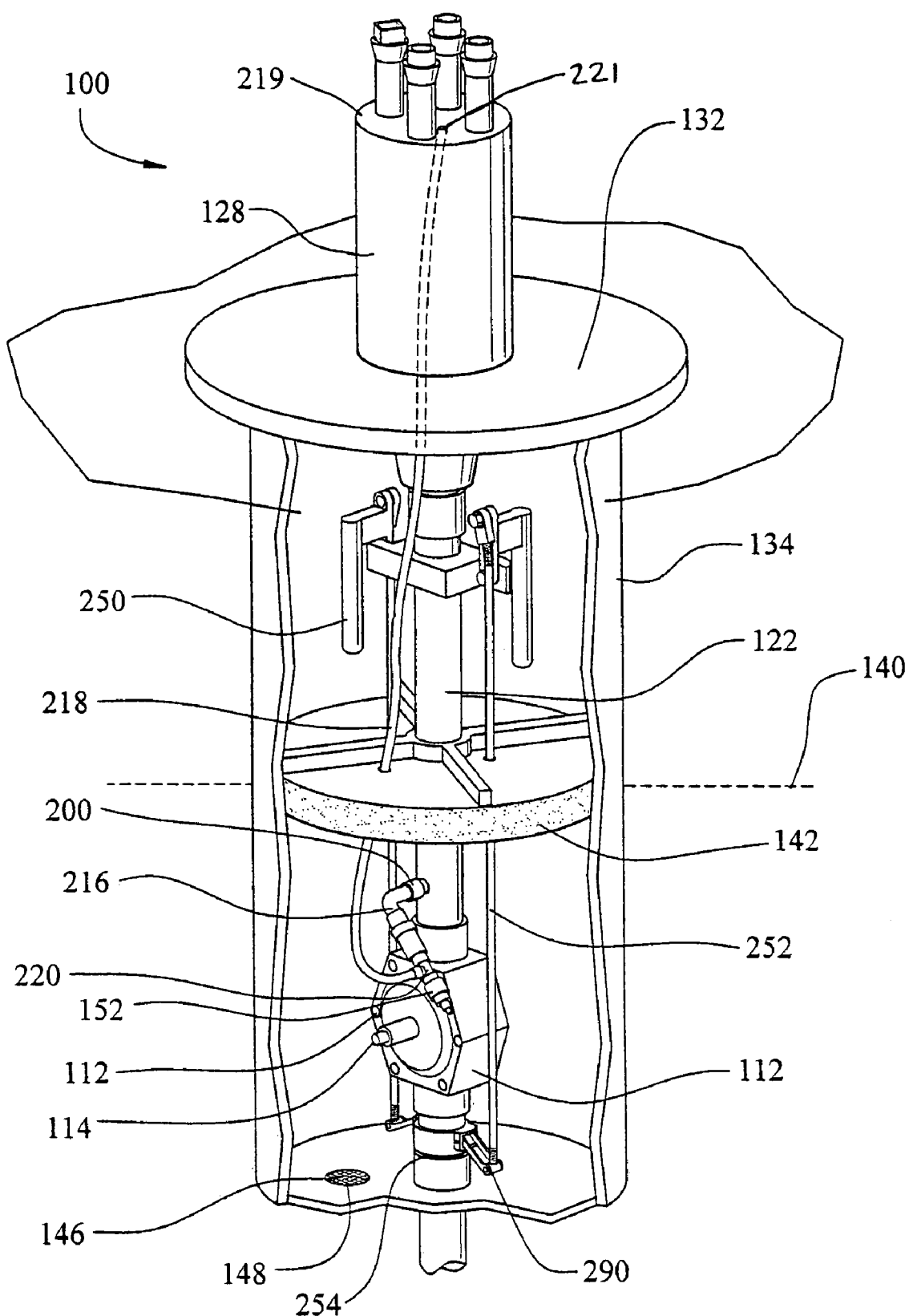
FIG. 14 is an isometric view of a water flushing system according to aspects of the present invention.

Therefore, in one embodiment, aspects of the present invention can include a pressure relief line 218 as shown in FIG. 14. The pressure relief line 218 can tie into the system by way of a t-fitting 220, for example, which would be placed between the double check valve 214 and the relief valve 152. The line 218 can be routed to a variety of places. For example, the relief line 218 can be connected into any of a number of places along the vertical piping 122. However, to avoid backflow concerns, the line 218 can alternatively be routed so that it outlets into a bulkhead portion 219 of the housing 128. In such case, an opening 221 can be included in the bulkhead portion by any of a number of method such as by drilling or punching. In such a configuration, any water flowing through the relief line 218 can be discharged with the rest of the water flushed from the system.

Figure 15:
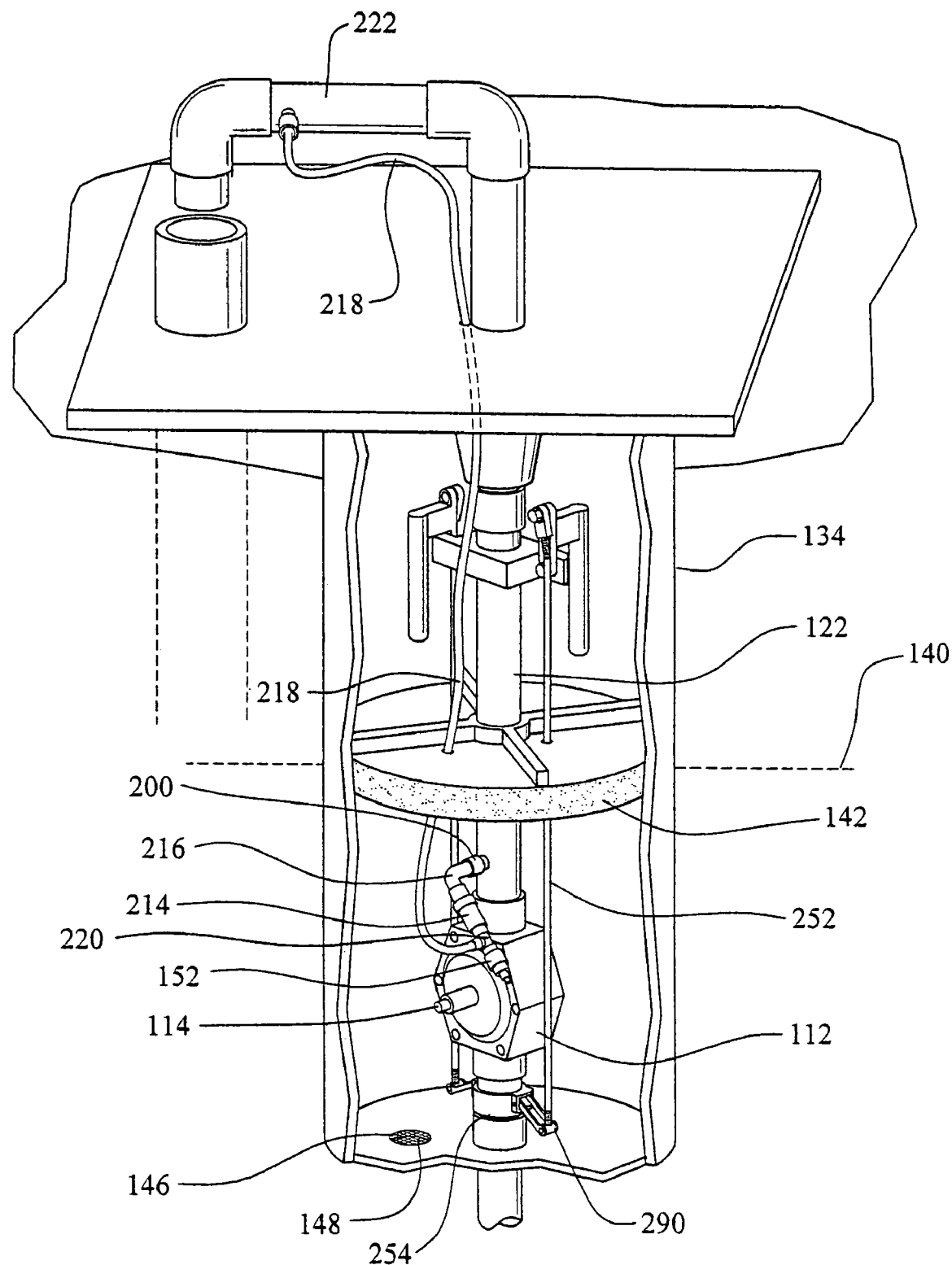
FIG. 15 is an isometric view of a water flushing system according to aspects of the present invention.

When the column-type system has a pipe-redirect discharge, the relief line 218 can be routed to an above-ground portion of the system such that any water carried in the line 218 will discharge out of the system by, for example connecting into a downwardly facing discharge pipe 222 such as shown in FIG. 15.

In short, there are numerous ways for providing freeze protection and backflow protection to the column-type system. While several embodiments according to aspects of the invention have been set forth above, they are only intended as examples as there are various other possibilities within the scope of the invention.

As noted earlier, a substantial portion of the column system 100 can be disposed beneath grade level 101 with many, if not all, of the functioning components situated below the frost line 140. Due to such an arrangement, access to the underground components, especially those below the frost line 140, can be rather challenging. Moreover, the need to access the system can arise frequently such as for inspection, maintenance (i.e. yearly battery replacement) and/or repair purposes.

Thus, aspects of the present invention relate to provide a latching system for allowing remote connection and disconnection of the water flushing apparatus 100. In addition, the latching system according to aspects of the invention enables a user to retrieve most if not all of water flushing system 100 without having to unearth or substantially disassemble the system. While the latching system is described in connection with water flushing system 100, the latching system according to aspects of the present invention is not so limited. Indeed, a latching system according to aspects of the invention can be used in any application in which a system or apparatus are located in underground, remote, confined and/or restrictive areas.

Figures 34, 35, 36:
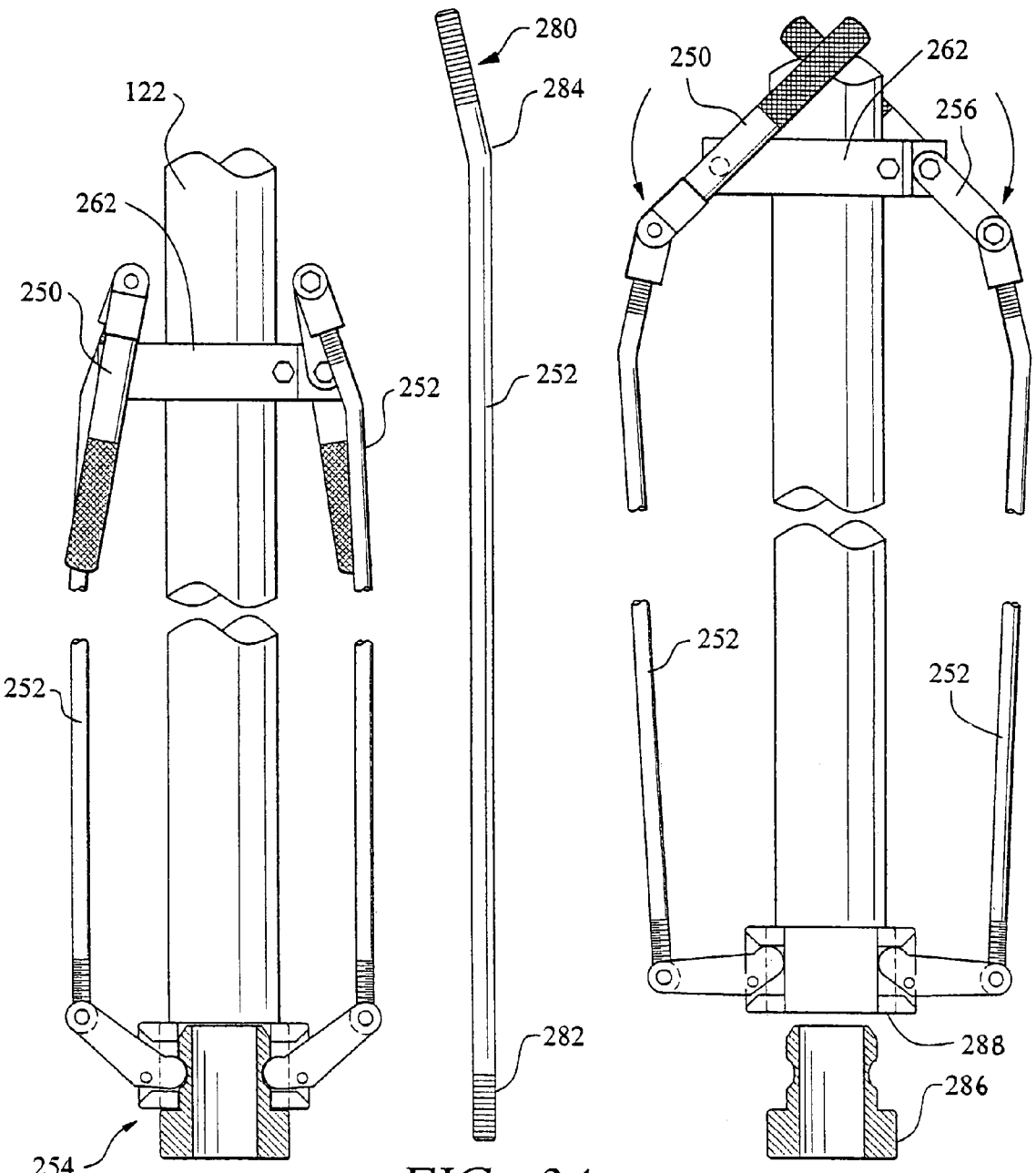
FIG. 34 is an elevational view of a connecting rod according to aspects of the present invention.
FIG. 35 is an elevational view of a latching system in a locked mode according to aspects of the present invention.
FIG. 36 is an elevational view of a latching system in an unlocked mode according to aspects of the present invention.

An example of a latching system according to aspects of the present invention is shown in FIGS. 35 and 36. The system can comprise one or more handles 250, one or more connecting rods 252 and a quick disconnect 254. Each of these components will be discussed in turn.

Figure 25:
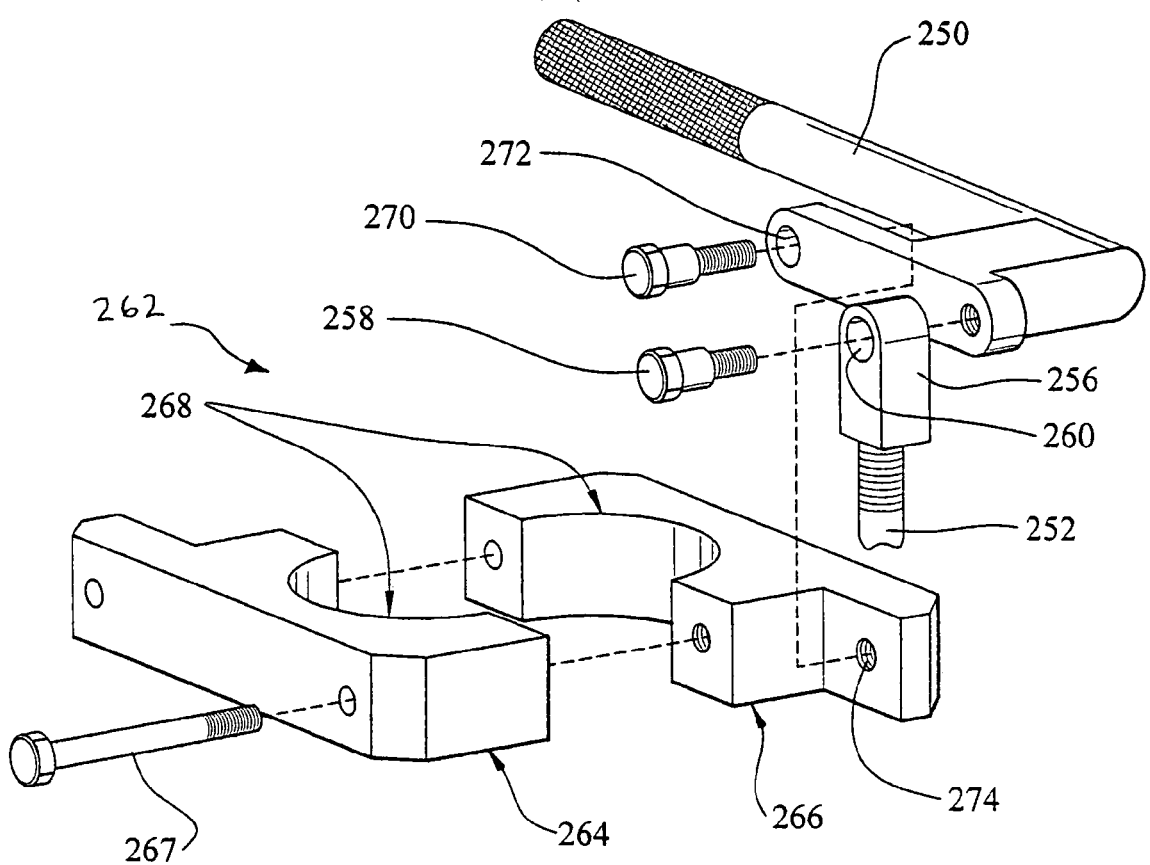
FIG. 25 is an isometric view of a handle and a handle mount according to aspects of the present invention.
Figure 26:
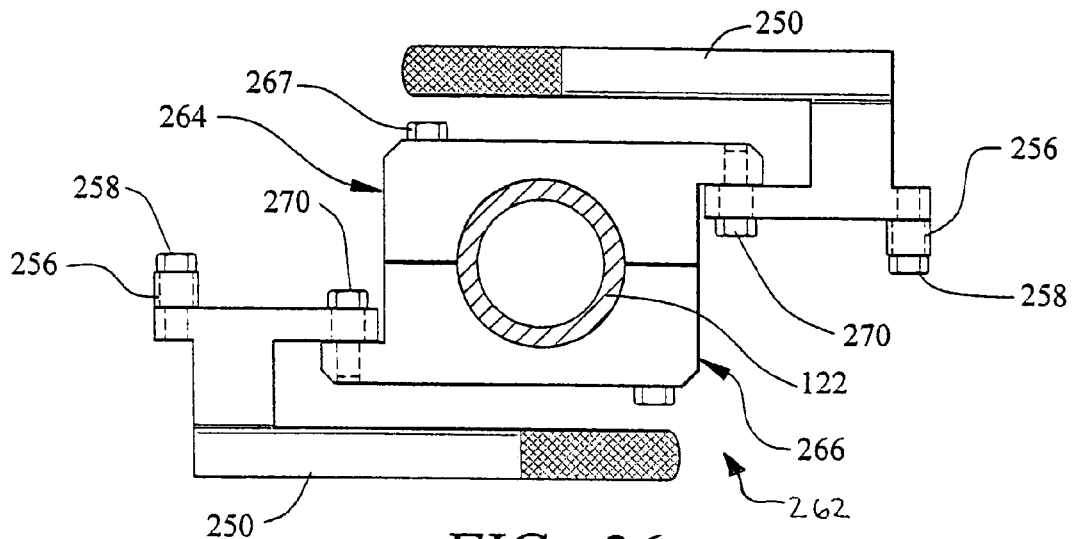
FIG. 26 is a top plan view of a handle and handle mount assembly according to aspects of the present invention.

One example of handles 250 according to aspects of the present invention are shown in FIGS. 25 and 26. The handles 250 can be any device that provides an interface for a user to remotely operate the quick disconnect component 254. The handles 250 can be a single piece or a multi-part assembly. The handles 250 can be made of any material and in one embodiment the handles 250 are made of metal. The handles 250 can provide an area for the user to grip such as a knurled shaft and can further include ergonomic features.

A part that can be associated with the handles is a connection block 256. The connection block 256 generally serves as the connection point between the handle 250 and a respective connecting rod 252. In one embodiment, there may not be a block 256 as the handle 250 may include integral structure in place of the block 256. However, when a block 256 is used, it is preferred if the block 256 is rotatably attached to the handle 250. Rotatably attached means that at least a portion of the block 256 can rotate relative to the handle 250 about at least one axis. One configuration for achieving rotatable attachment is for the block 256 to be secured to the handle 250 using a shoulder bolt 258. In such case, the block 256 can include an opening 260 to allow passage of the shoulder bolt 258 or other elongated member or fastener, which can screwed into or otherwise anchored to the handle 250.

The block 256 can have any configuration such a being generally rectangular, as shown in FIG. 25, or any other shape such as triangular, polygonal oval cylindrical, to name a few. The block 256 can be made of any of a variety of materials including metals and plastics. The block 256 can provide features for attaching the block 256 to other system components. For example, the block 256 can provide a threaded hole for receiving a threaded end of a connecting rod, or, as noted above, the block 256 can include a pass through openings to accommodate various fasteners.

The handles 250 and block 256 can be attached to the column system 100 in a variety of ways. For example, the handles 250 can be attached directly or indirectly to any part of the column system such as the vertical piping 122 or one of the housings 134, 118. In one embodiment, the handles 250 can be attached to the column system so as to be removed along with the system after the system is disconnected. Preferably, the handles 250 are generally associated with the system so as to be located in a user accessible region of the system or apparatus.

The handles 250 can be attached to any component of the column system. In one embodiment, shown in FIG. 26, the handles 250 can be attached to the vertical piping 122 by way of a handle mount 262. The handle mount 262 can have numerous configurations. For example, the handle mount 262 can be integral with the vertical piping itself 122 or it can be a separate piece that can comprise a single part or an assembly. One example of a handle mount 262 according to aspects of the invention is shown in FIGS. 25 and 26. As shown, the handle mount 262 can be a two piece construction having first and second halves 264,266. Each half 264,266 can have a recess 268 so that when the halves 264,266 are secured together, such as by bolts 267, a passage is formed therebetween through which a component such as the vertical piping 122 can pass. The recesses 268 in each half 264,266 can be any shape, but preferably each half mount 264,266 includes a generally semi-circular recess 268. Preferably, the halves of the mount 264,266 are identical so as to reduce the number of unique parts of the system, but they need not be identical. The mount 262 can be made of a plethora of materials including metals and plastics; in one embodiment, the handle mount 262 is made of the same material as the handle 250.

The handles 250 can be attached to the handle mount 262 and/or vertical piping 122 in a variety of manners. In one embodiment, the handles 250 can be rotatably attached to the handle mount 262. Rotatable attachment means that at least a portion of the handle can rotate relative to the handle mount about at least axis. In the way of an example, rotatable attachment can be achieved by securing the handle 250 to the handle mount 262 using a shoulder bolt 270. The shoulder bolt 270 can pass through a hole 272 in the handle 250 and screw into a threaded hole 274 provided in the mount 262. Thus, a user can turn the handle 250, causing the handle 250 to rotate about the shoulder screw 270 while the handle mount 262 remains stationary.

The latching system according to aspects of the present invention further can include connecting rods 252. An example of a connecting rod 252 can be seen in FIG. 34. The rods 252 can be made of any material but stainless steel is preferred. The rods 252 can be generally hollow or solid, and can have any of a number of cross-sections such as generally circular, polygonal, rectangular, square, oblong. The connecting rods 252 include a proximal end 280 and a distal end 282. The relative terms proximal and distal relate to the spatial relation between a particular end of a connecting rod 252 and a user, the proximal ends 280 being closer to the user, such as at the near the top of the water flushing system, than the distal ends 282.

Each end 280, 282 of the connecting rod 252 can be configured for attachment or securement to the handles 250 and the quick connect/disconnect 254. For example, at least one end can provide a threaded male end. As shown in FIG. 34, both the proximal and distal ends 280, 282 have external threads. In one embodiment of the latching system, shown in FIGS. 35 and 36, the proximal end 280 of the connecting rods 252 can be attached to the handles 250 and/or block 256; the distal end 282 of the connecting rods 252 can be attached to a portion of a detachable coupling 254 such as a quick connect/disconnect.

The rods 252 can be connected to the handle 250 and/or detachable coupling 254 in a variety of manners such as by welding, one or more fasteners, threaded engagement, or in a ball and socket relationship. Preferably, the proximal end 280 of the rods 252 include external threads for threadably engaging the block portion 256 of the handle. Thus, the connecting rod 252 can rotate with the block 256 as it rotates. Similarly, the distal end 282 of the connecting rods 252 can have numerous configurations for attachment to the quick connect/disconnect 254. In one embodiment, the distal end 282 can be provided with external threads for threaded engagement with a portion of the quick connect/disconnect 254. In another embodiment, the connecting rods 252 can provide handle-like structures (not shown) at its proximal end 280 to as to eliminate the need for separate handle members 250.

In one embodiment, the connecting rods 252 can be generally straight. However, it is preferred that the connecting rods 252 include a bend 284 near the proximate end 280 of the rod 252 as shown in FIG. 34. With respect to vertical, the rods 252 can be bent from about 14 degrees to about 26 degrees and, more particularly, from about 14 degrees to about 20 degrees and, even more particularly, at about 15 degrees. The bends 284 can be formed in any of a variety of manners such as by hand, pliers, or a tube bending apparatus. The bent rod configuration can provide advantages over a straight rod when locking the quick connect/disconnect 254 because the bend 284 can provide additional locking or clamping force as the user moves the handles 250 so as to lock the quick connect/disconnect 254.

Figure 27:
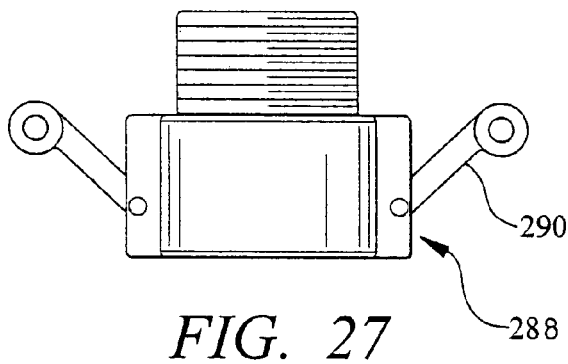
FIG. 27 is a side elevational view of a female cam portion of a cam lock device according to aspects of the present invention.
Figure 28:
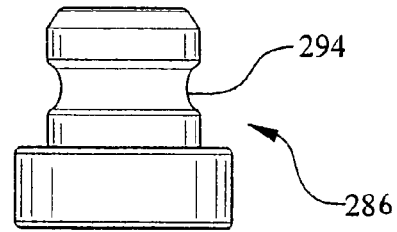
FIG. 28 is a side elevational view of a male connector portion of a cam lock device according to aspect of the present invention.
Figure 29:
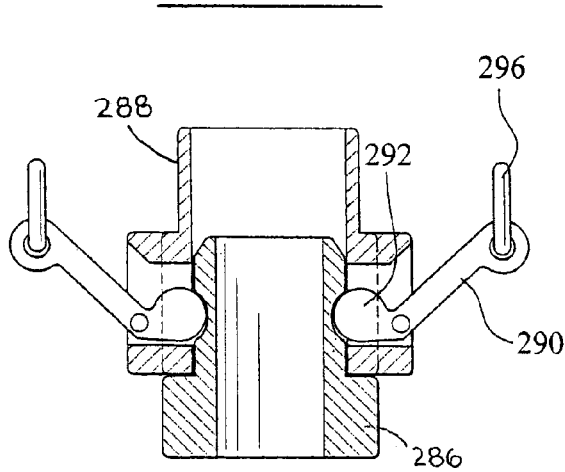
FIG. 29 is a cross-sectional view of a cam lock device in a locked mode according to aspects of the present invention.

As noted earlier, the latching system according to aspects of the present invention can further include a quick-connect/disconnect 254. One example of such a device is a cam lock that is shown in FIGS. 27 and 28; however, the quick connect/disconnect 254 can have a variety of forms.

As noted earlier, the column system can be secured to a water distribution line by way of a quick connect/disconnect 254. The quick connect/disconnect 254 can be anything that can detachably couple two components together. At least a portion of the quick connect/disconnect 254 can be a part of a component. That is, a localized area of a component can include features that would allow it to lock and unlock to other components. With respect to the column-type flushing system, the quick connect/disconnect 254 is used to attach the water inlet piping of the system to an underground water distribution system.

Figure 30:
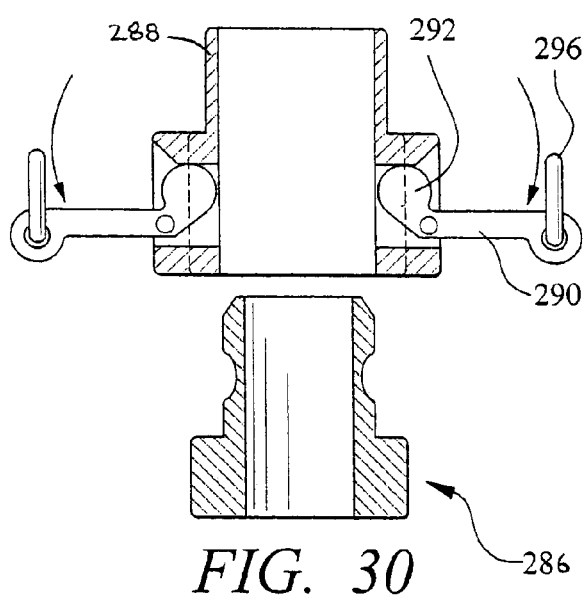
FIG. 30 is a cross-sectional view of a cam lock device in an unlocked mode according to aspects of the present invention.

One example of a quick connect/disconnect 254 can be a cam lock as are known in the art. The cam lock 254 can generally comprise a male portion 286 (FIG. 28) and a female portion 288 (FIG. 27). The male portion 286 can be matingly received in the female portion 288. The male component 286 can be coupled, for example, to an end of a pipe from the underground water distribution system; the female coupling 288 can be secured, for example, to the inlet piping of the column-type water flushing system. The cam lock 254 provides one or more handles 290 that can rotate between locked and unlocked positions. In the locked position, shown in FIG. 29, a cam portion 292 of the handle can extend partially into the interior of the female component 288 so as to lockingly engage a bearing surface 294 on the male component 286. The bearing surface 294 can have a reduced diameter with respect to the adjacent areas of the male portion 286. In the unlocked position, as shown in FIG. 30, the cam portions 292 of the handles do not engage the male component 286 so as to permit the male and female components 286, 288 to be separated from each other. In some embodiments, the cam lock handles 290 can include one or more rings 296 for a user to grab.

As noted earlier, the distal end 282 of the connecting rods 252 are attached to the quick connect/disconnect 254 device so as to allow a user to selectively lock and unlock the device. For example, the connecting rods 252 can be attached to the handles 290 of the cam lock 254. There are numerous ways for attaching the connecting rods 252 to the handles 290 of the cam lock 254 such as by welding, brazing or adhesives. Preferably, the connecting rods 252 are rotatably attached to the handles 290 of the cam lock 254, which can include the ring 296. Rotatably attached means that at least a portion of the connecting rod 252 can rotate about at least one axis relative to at least a portion of the handle 290 of the cam lock 254.

In accordance with aspects of the present invention, rotatable attachment can be achieved by modifying a standard cam lock device 254. For example, one or more parts can be added to the handle 290 of the cam lock 254. One such assembly of parts can be seen in FIG. 31. The assembly can include first and second side members 300 a bridge member 302 and an rod attachment member 304. Both the first and second side members 300 include a first opening 306 for receiving the bridge member 302 and a second opening 308 for receiving the attachment member 304. The side members 300 can be made of metal and can be generally flat pieces.

The bridge member 302 can also be a flat piece of metal with any conformation. As shown, the bridge member 302 can be generally rectangular. The rod attachment member 304 generally provides a central attachment portion 310 that can include, for example, a threaded hole 312 for attaching the distal end 282 of a connecting rod 252. Axles 314 can extend from each side of the central attachment portion 310. The rod attachment member 310 can be disposed between the side members 300 such that the axles 314 are received within the second openings 308 of the side members 300 such that the rod attachment member 310 can rotate therein. Moreover, the bridge member 302 can extend between the first openings 306 in the side members 300 as well as a slot 316 in the cam lock handle 290. The slot 316 can be a preexisting slot used to retain the ring 296 (the ring being removed in this embodiment) or it can be added by, for example, machining or waterjet.

Figures 31, 32:
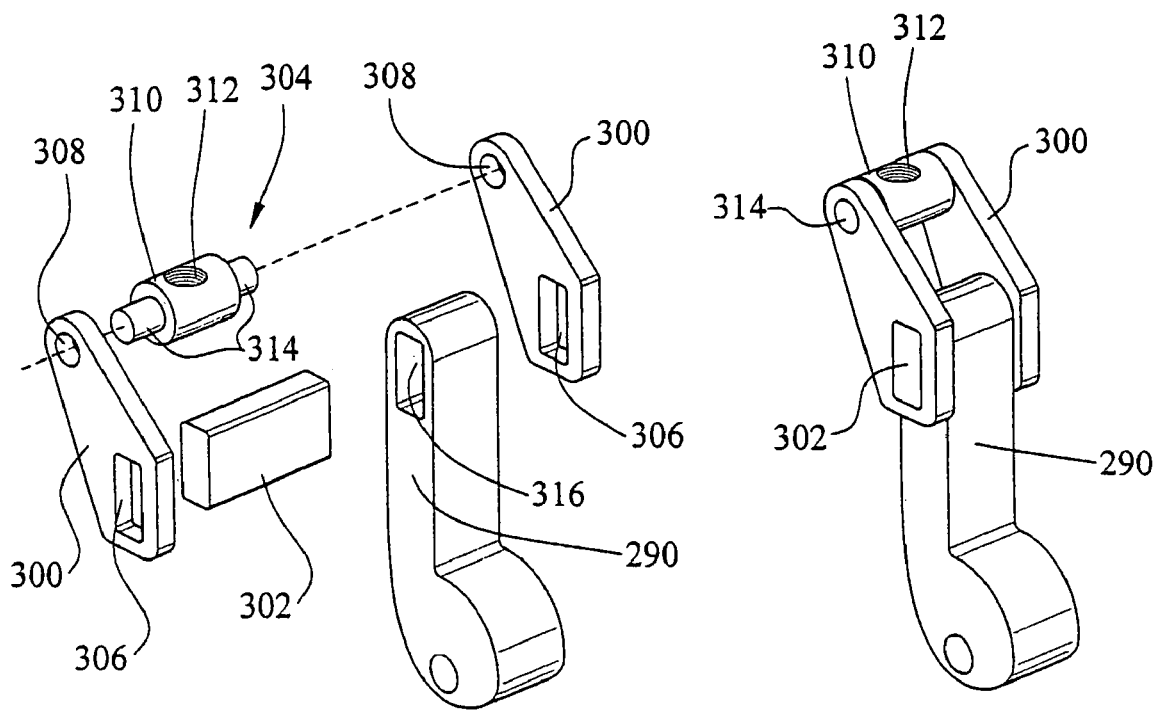
FIG. 31 is a exploded isometric view of a modified cam lock handle according to aspects of the present invention.
FIG. 32 is an isometric view of a modified cam lock handle according to aspects of the present invention.
Figure 33:
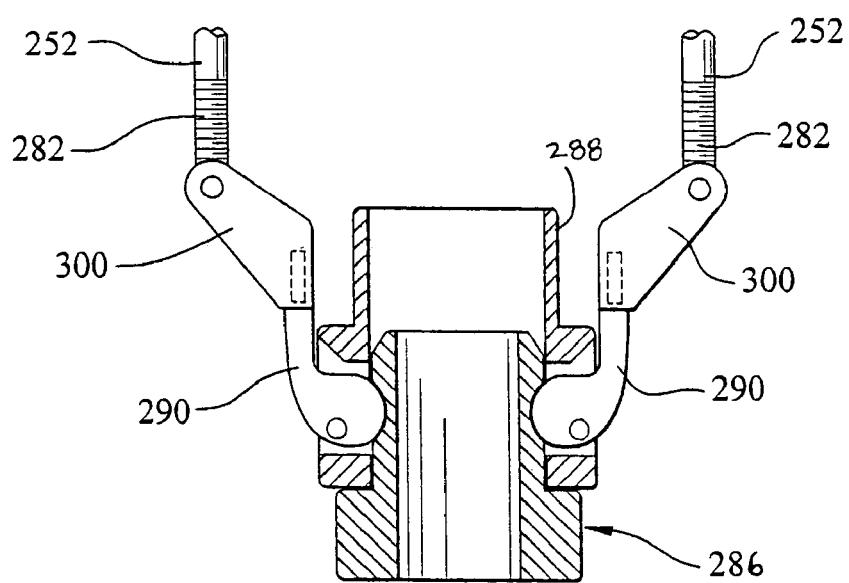
FIG. 33 is a cross-sectional view of a cam lock device with modified handles according to aspects of the present invention.

Once all the pieces are generally assembled, the bridge portion 302 can be secured to the side portions 300 in any of a variety of manners such as by welding or brazing. When finished, the assembly can appear as shown in FIG. 32. Again, this is only one manner in which the handles 290 of the cam lock 254 can be configured for attachment to the connecting rods 252.

Further, when the cam lock 254 includes two or more handles 290, the handles 290 can be configured in an substantially identical manners (see FIG. 33) or the handles 290 can be configured in completely different manners for attaching to the connecting rods 252. For example, one cam lock handle 290 can be welded to the connecting rod 252 whereas the other cam lock handle 290 can be secured to the connecting rod 252 by threaded engagement. Yet another possibility is to secure one of the connecting rods 252 to the ring 296 that can be provided on the handles 290 of the cam lock 254.

Having described the individual components of a latching system according to aspects of the invention, one manner in which these components can be assembled will be described below. The described assembly is only intended as an example as the assembly can occur in just about any sequence and not every step described below need occur.

The two halves 264, 266 of the handle mount 262 can be joined together so as to clampingly surround the vertical piping 122 as shown in FIG. 26. The handle mount halves 264, 266 can be joined in any of a variety of manners such as by welding, adhesives, or fasteners such as bolts 267. Next, the two handles 250 can be rotatably attached to the handle mount 262 using, for example, shoulder bolts 270. Then, the block 256 can be rotatably attached to each of the handles 250 such as by shoulder bolts 258.

Each block 256 can be provided with threaded holes (not shown) into which the threaded proximal ends 284 of the connecting rods 252 are received in threaded engagement. Additional securement devices such as thread lock, adhesives or welding may be used to further establish the connection between the connecting rods 252 and the block 256. Once attached, at least the proximal ends 282 of the connecting rods 252 can rotate with the block 256 relative to the handles 250.

Next, the distal ends 284 of the connecting rods 252 can be secured in threaded engagement with the holes (not shown) provided in the handles 290 of the female portion 288 of the cam lock device 254. Alternatively, the rods 252 may be secured to the handle 290 directly or to the rings 296 provided with the cam lock device 254. Preferably, the connecting rod 252 is connected to at least a portion of the handle 290 of the cam lock device 254 can rotate like, for example, rod attachment member 310 in the case of modified handles 290.

One manner in which the latching system can be used in connection with the column-type water flushing system will now be described. A user may wish to access certain portions of the flushing system that are disposed below ground. For example, the user may need to replace the control valve 112. In such case, a user can cut off the water supply from the main distribution line through a curb stop 113 (FIG. 10). After cutting off the water supply, a user may run the flushing system to purge any residual water out of the system 100.

Next, the user can remove any components of the flushing system that restrict access to the latch system handles 250 such as the housing 118 as well as cap 126. Once accessible, the handles 250 can be turned by a user in a manner so as to unlock the cam lock 254. When the user turns a handle 250, the motion of the handle 250 can be transmitted to the handles 290 of the cam locks 254 by way of the connecting rods 252. Thus, the cam lock handles 290 can be moved from their locked position (FIG. 35) to their unlocked position (FIG. 36).

After the user has moved both handles 290 of the cam lock 254 into the unlocked position, the user can manually retrieve the entire or substantially all of the water flushing apparatus. For example, the user can pull upward on the handles 250 and the entire unit will slide out of the underground housing 134. Then a user can perform the necessary repairs or maintenance on the system.

Once the repair or maintenance is completed, the latching system can be used to reattach the water flushing system 100 to the main water distribution line. In such case, the water distribution system can be lowered into the housing 134 so that the female cam lock 288 receives the corresponding male receptacle 286 on the end of the water distribution system. Once properly in position, the handles 250 can be turned which result in a corresponding movement of the cam lock handles 290 so as to lock the cam lock 254. When moving the handles to a locked, the bend 284 in the connecting rod 252 can assist by providing additional force in bringing the cams 292 into locked engagement with a surface 294 of the male connector 286.

While the latching system has been described in connection with a water flushing system, the latching system according to aspects of the invention can be applied to any system or apparatus in which it is difficult to access at least a portion of the system or apparatus such as when the system or apparatus are disposed in a confined space or are subterranean.

In connection with the column-type water flushing system, aspects of the invention can further relate generally to the treatment of at least a portion of the water being flushed from the system. In one embodiment, the aspects of the invention can relate to dechlorination of the water, which can be accomplished in various manners. Two examples of dechlorination systems will be discussed below—one manner is especially suited for the pipe-redirect system and the other manner is especially suited for the cap-redirect system. While discussed in terms of dechlorination, the water treatment system below can be used to treat the flushing water in a variety of ways that are within the scope of the invention.

With respect to the pipe-redirect type of column system, aspects of the dechlorination system discussed in connection with the box system are equally applicable here as would be appreciated by one skilled in the art. For example, as shown in FIG. 1, inlet tubing 86 can be connected into the discharge piping 26 such that a portion of discharge water will be routed to a water treatment container 80 (see also FIG. 8) such as has been previously discussed. After flowing through the container 80, the treated water can then flow into back into the discharge piping. For example, the inlet and outlet tubing for the water treatment container could connect into any portion of the above ground piping shown in FIG. 10.

However, with respect to the cap-redirect configuration, aspects of the present invention can provide a different configuration for dechlorinating at least a portion the water being discharged. In one respect, it is desirable to provide a water treatment device such as a dechlorinator in a form that will not require substantial alteration of the basic cap-redirect design.

Figures 37, 38:
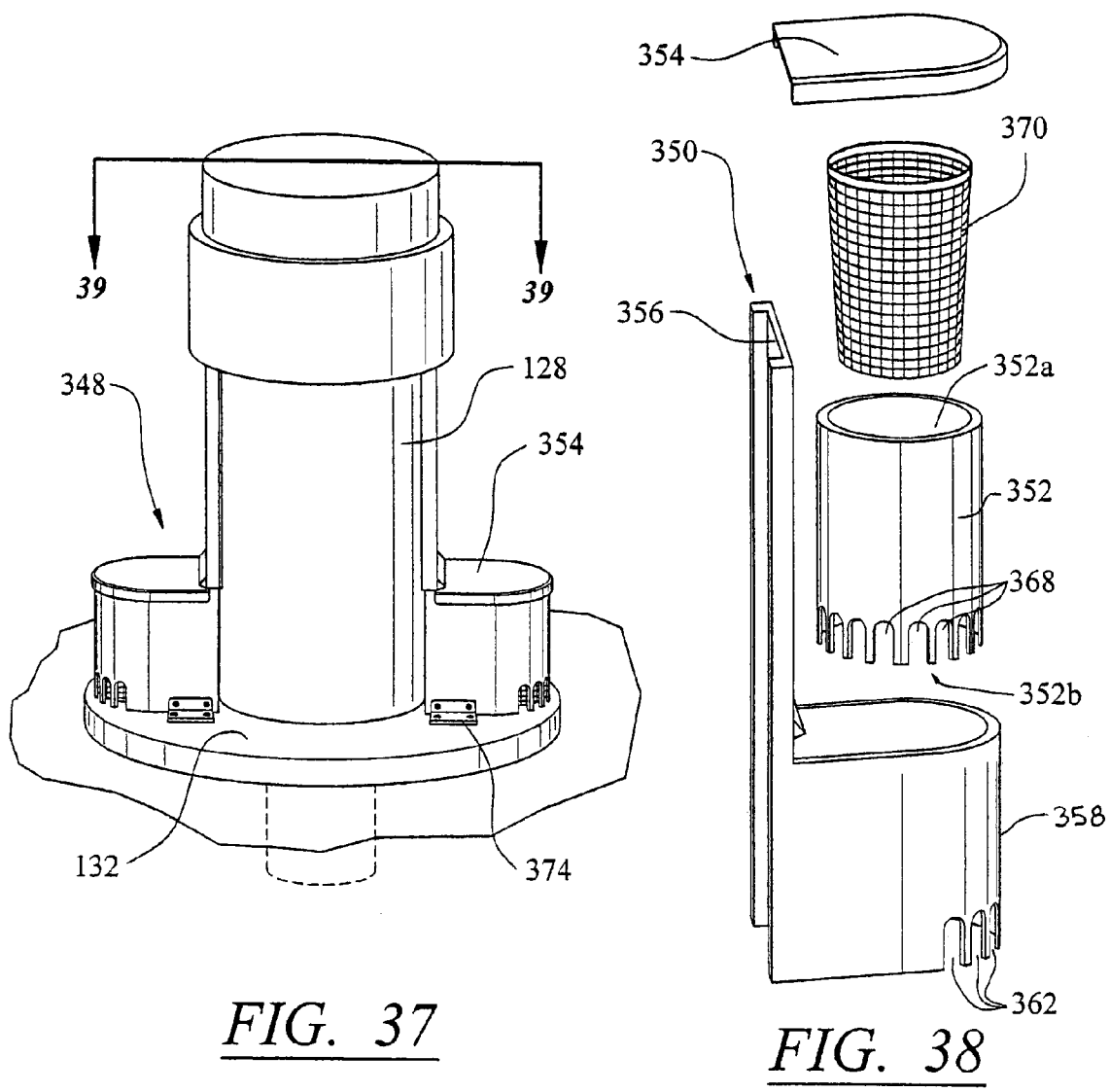
FIG. 37 is an isometric view of a water flushing system with water treatment/dechlorination devices according to aspects of the present invention.
FIG. 38 is an exploded isometric view of a water treatment/dechlorination device according to aspects of the present invention.
Figure 39:
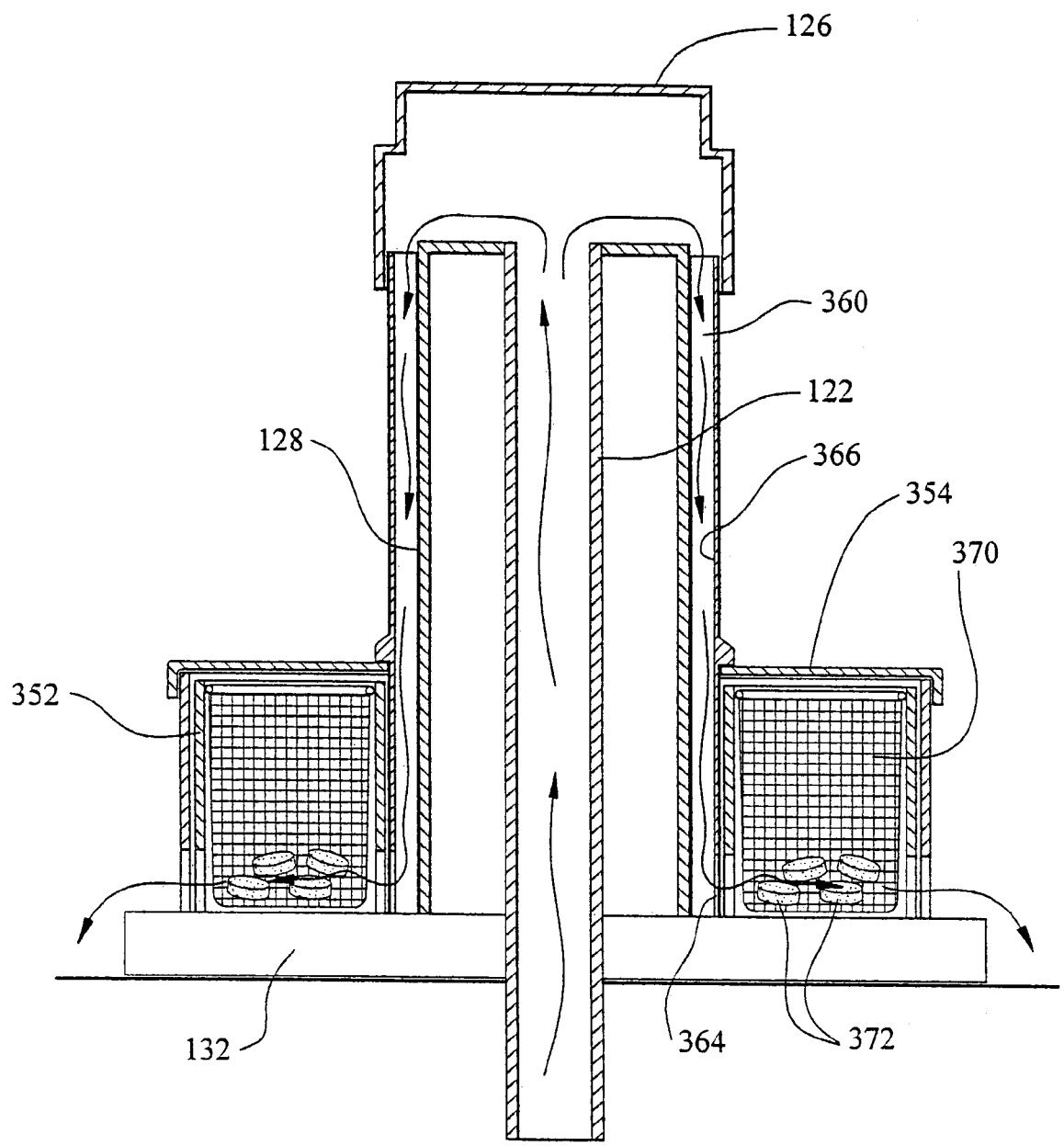
FIG. 39 is a cross-sectional view of a water flushing system with water treatment/dechlorination devices according to aspects of the present invention, taken along line 39-39 of FIG. 37.

One example of such a system is shown in FIGS. 37-39. The shown assembly can include a number of parts such as a router 350, a container 352 and a cap 354. These and other components will be discussed in turn.

The router 350 can include a generally vertical channel portion 356 and a treatment chamber 358. The treatment chamber 358 can extend generally forward and transverse to the channel portion 356. Preferably, the channel portion 356 matingly interfaces with at least a portion of the outer surface of the housing 128 so as to define a passage 360. The router 358 can sized so as to extend substantially along the above-ground length of the housing 128. The chamber portion 358 is generally hollow and can be in any of a number of configurations. For example, as shown in FIG. 38, the chamber 358 can be generally U-shaped and can include a series of openings 362 along at least a portion of its lower edge. The chamber portion 358 and the channel portion 356 can be in fluid communication by one or more openings or passages 364 provided between the two portions. For example, as shown in FIG. 39, at least a portion of the back wall 366 of the channel portion 356 does not extend the entire length of the part. Thus, fluid can pass into the chamber portion 362.

The container member 352 of the water treatment/dechlorination assembly can have any of a number of conformations and may be made of any of a number of materials including metals and plastic like PVC. Preferably, the container 352 is made of a material that is compatible with any substance held within. In one embodiment, the container 352 is made of PVC and is generally cylindrical. The container 352 is open at each of its upper and lower ends 352a, 352b, and at its lower end 352b can further include a series on openings 368 along at least a portion of its periphery. In one embodiment, the openings 368 can extend about the entire periphery as shown in FIG. 38. Alternatively, a group of openings 368 can be provided on opposite sides of the container 352. The cutouts can be any shape and size. The container 352 may further include a wire mesh 370 for trapping any treatment substance 372 within the container 352 to make it more difficult for the treatment substance 372 to be washed through the openings 368, 362 in the container 352 and chamber 358. The mesh can be disposed in the container in multiple ways. For example, the wire mesh 370 can simply be placed in the container 352 without fixing it to the container 352 in any way. Thus, the wire mesh can be freely placed in and taken out of the container 352. In another embodiment, the wire mesh 370 can be pushed into the container 352 from either side of the container 352a, 352b and/or can be glued in place.

The wire mesh 370 can be made of a number of materials such as metals and plastics. The mesh 370 can also have a wide range of configurations. In one embodiment, the wire mesh 370 can be generally cylindrical. The height of the mesh 370 can vary as well. For example, as shown in FIG. 39, the wire mesh 370 can be substantially the same height as the container 352. In another embodiment, the wire mesh can be a relatively shallow piece, possibly as substantially the same height or slightly taller than the openings 368 in the container 352.

As discussed earlier, the treatment substance 372 can be almost anything and various regulations can dictate what substance or substances are needed. When the discharging water must be dechlorinated, the substance 372 can be, for example, sodium sulfite, which may be provided in any form including tablets. In other cases, the substance can be vitamins.

The assembly can include a cap 354 for covering the open top of the container 352a and the chamber portion 358 of the router 350. Can be made of any materials but plastic is preferred. The cap 354 can be conformingly fitted over the open top.

One manner of assembling the above components will be described. The router 350 can be placed substantially adjacent to the housing 128 such that the cap 126 is substantially adjacent to an upper end of the channel portion 356 of the router 350. In another embodiment, the cap 126 can overlap a portion of the channel 356 as shown in FIG. 39. The assembly can be held in place by securing the assembly to the splash guard by, for example, an L-shaped bracket 374.

Next, the wire mesh 370 can be placed in the container 352, which can then be filled with one or more treatment substances 372. Container 352 can be placed in the chamber 358 of the router 350 and then covered with the cap 354. As can be appreciated from the above, the installation of the water treatment assembly requires minimal modification to the cap-redirect system.

Now one manner in which the system can be used will be described. During a flushing operation, the cap 126 directs water downwardly out of the system. Some of the discharged water will flow onto the splash guard 132 and then into the soil. However, a portion of the discharged water will flow into the passage 360 defined between the channel portion 356 of the router 350 and the outer wall of the housing 128. The water flowing down the passage 360 will flow into the chamber portion 358 of the router 350 by way of an opening 364 provided in the channel portion 356 of the router 350.

Once in the chamber portion 358, the water can flow into the container 352 through its lower openings 368 and scour against the water treatment tablets 372. The water can ultimately exit the assembly through the openings 362 in the chamber portion 358 of the router 350. As water exits the dechlorination assembly, it can mix with the other flushing water so as to effectively treat the water that did not flow through the water treatment assembly.

The amount of dechlorination can be regulated at least by the number of dechlorination assemblies 348 that are attached about the base of the housing 128. In one embodiment, a single dechlorination assembly 348 can be used; however, in other embodiments, there can be two or more (as shown in FIG. 37). The maximum number of assemblies 348 that can be installed depends at least upon the size of the assembly and the size of the housing. In one embodiment, there can be up to four dechlorination assemblies spaced around the outer periphery of the housing 128.

Alternatively, the amount of treatment can also be controlled through the series of holes 362 located at the base of the router 358. By plugging one or more of these holes 362, the amount of water flowing across the dechlorination tablets 372 can be adjusted. Obviously, if none of the holes 372 are plugged, then the greatest amount of water is allowed to scour the tablets, thereby releasing the greatest amount of chemical.

In summary, there are several aspects according to the present invention that can be used in connection with column-type system. Aspects include at least freeze protection, backflow prevention, various specialty fitting and valves, dechlorination and other water treatment systems and a retrieval system.

It will of course be understood that the invention is not limited to the specific details described herein, which are given by way of example only, and that various modifications and alterations are possible within the scope of the invention as defined in the following claims.

What is claimed is:

1. A remote latch system for a partially below ground water flushing apparatus comprising:
a pressurized subterranean water distribution system;
a water flushing apparatus having a flow controlled passage with an inlet adapted for fluid connection to the pressurized water distribution system, a first portion of the water flushing apparatus being above ground and including an outlet, a second portion of the flow controlled passage being below ground, wherein water from the water distribution system exiting the outlet is directed downwardly toward the ground;
a flow control valve disposed along the flow controlled passage for selectively permitting and prohibiting the flow of pressurized water through the flow controlled passage;
a programmable controller operatively associated with the flow control valve, wherein the controller regulates the flow of pressurized water received from the water distribution system through the flow controlled passage by activating and deactivating the flow controlled valve on a predetermined timed basis;
a quick connect/disconnect coupling for detachably coupling the pressurized subterranean water distribution system and the inlet of the water flushing apparatus, the quick connect/disconnect coupling having a locked mode, in which the pressurized subterranean water distribution system and the inlet of the water flushing apparatus are coupled, and an unlocked mode, in which the pressurized subterranean water distribution system and the inlet of the water flushing apparatus are decoupled, wherein the second portion of the water flushing apparatus extends from the quick connect/disconnect coupling to the first portion, wherein the second portion is distributed in a generally vertically elongated manner;
an elongated first connecting rod having a proximal end and distal end, an elongated second connecting rod having a proximal end and a distal end, the distal end of each connecting rod being operatively connected to the quick connect/disconnect coupling so as to permit manipulation, remotely at the distal end, of the quick connect/disconnect coupling between the locked and unlocked modes, whereby in the unlocked mode the flushing system can be retrieved as a unit from below ground by way of the connecting rods, wherein the proximal end of each connecting rod is operatively connected to a respective handle, wherein each handle is rotatably mounted on the water flushing apparatus,
wherein the flow control valve, the quick connect/disconnect coupling, the first and second connecting rods and the handles are located below ground, and
a below ground housing substantially enclosing the second portion of the water flushing apparatus, the flow control valve, the first and second connecting rods and the handles.

2. The system of claim 1 wherein at least one of the connecting rods includes a substantially straight portion and a bent proximal end, wherein the proximal end is bent from about 14 degrees to about 26 degrees relative to the substantially straight portion of the connecting rod.

3. The system of claim 1 wherein the quick connect/disconnect coupling is a cam lock.

4. The system of claim 3 wherein the quick connect/disconnect includes a male connector and a female connector, wherein the male connector is integral with the water distribution system and the female connector is integral with the water flushing apparatus.

5. The system of claim 4 wherein the female connector includes a pair of cam handles for selectively lockingly engaging the male connector, wherein the distal end of each connecting rod is operatively connected to a respective cam handle.

6. The system of claim 1 wherein the quick connect/disconnect coupling is located at a depth of at least 3 feet below the ground.

7. The system of claim 1 further including an above-ground housing at least partially enclosing the first portion of the water flushing apparatus.

8. The system of claim 7 further including a cap operatively positioned to redirect water exiting the outlet downwardly toward the ground and about the exterior of the above-ground housing.

9. The system of claim 7 further including a splash guard substantially at ground level and separating the above ground housing and the below ground housing, whereby erosion of the ground due to water exiting from the outlet is minimized.

10. The system of claim 1 wherein the first portion is configured such that the outlet is positioned downwardly toward the ground.

* * * * *